United States Patent
Nagao et al.

(10) Patent No.: US 10,023,530 B2
(45) Date of Patent: Jul. 17, 2018

(54) DIAMINE, POLYAMIC ACID, AND POLYIMIDE

(71) Applicant: NISSAN CHEMICAL INDUSTRIES, LTD., Chiyoda-ku (JP)

(72) Inventors: Masato Nagao, Funabashi (JP); Mitsumasa Kondo, Funabashi (JP); Kentaro Nagai, Funabashi (JP)

(73) Assignee: Nissan Chemical Industries, Ltd., Chiyoda-ku (JP)

(*) Notice: Subject to any disclaimer, the term of this patent is extended or adjusted under 35 U.S.C. 154(b) by 20 days.

(21) Appl. No.: 15/031,669

(22) PCT Filed: Oct. 22, 2014

(86) PCT No.: PCT/JP2014/078138
§ 371 (c)(1),
(2) Date: Apr. 22, 2016

(87) PCT Pub. No.: WO2015/060359
PCT Pub. Date: Apr. 30, 2015

(65) Prior Publication Data
US 2016/0264520 A1    Sep. 15, 2016

(30) Foreign Application Priority Data

Oct. 23, 2013 (JP) ................ 2013-220592
Dec. 27, 2013 (JP) ................ 2013-273459
Sep. 12, 2014 (JP) ................ 2014-186809

(51) Int. Cl.
| | | |
|---|---|---|
| C07C 271/20 | (2006.01) |
| C07C 271/16 | (2006.01) |
| C07C 271/22 | (2006.01) |
| C08G 73/10 | (2006.01) |
| G03F 7/038 | (2006.01) |

(52) U.S. Cl.
CPC .......... *C07C 271/20* (2013.01); *C07C 271/16* (2013.01); *C07C 271/22* (2013.01); *C08G 73/105* (2013.01); *C08G 73/1071* (2013.01); *C07C 2603/18* (2017.05); *G03F 7/0387* (2013.01); *H01L 2924/12044* (2013.01); *Y10T 428/10* (2015.01); *Y10T 428/1005* (2015.01)

(58) Field of Classification Search
CPC ......... H01L 2924/12044; G03F 7/0387; Y10T 428/10; Y10T 428/1005
See application file for complete search history.

(56) References Cited

U.S. PATENT DOCUMENTS

2011/0080547 A1    4/2011  Matsumori et al.

FOREIGN PATENT DOCUMENTS

| | | |
|---|---|---|
| CN | 102959461 A | 3/2013 |
| JP | WO2010/050523 A1 | 5/2010 |
| JP | 2011-76009 A | 4/2011 |
| JP | 2012-193167 A | 10/2012 |
| JP | WO 2012133829 * | 11/2012 |

OTHER PUBLICATIONS

USPTO structure seach, Sep. 2017.*
USPTO inventors strucure seach, Sep. 2017.*
International Search Report dated Jan. 20, 2015 in PCT/JP2014/078138.

* cited by examiner

*Primary Examiner* — Gregory Listvoyb
(74) *Attorney, Agent, or Firm* — Oblon, McClelland, Maier & Neustadt, L.L.P.

(57) ABSTRACT

To provide a novel diamine, and a polyimide precursor and a polyimide using it. A diamine represented by the formula (1):

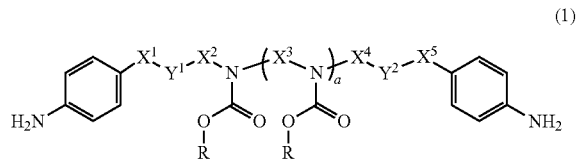

(1)

wherein each of $X^1$ and $X^5$ which are independent of each other, is a single bond or the like; each of $X^2$ and $X^4$ which are independent of each other, is $—CH_2—$ or the like; $X^3$ is a $C_{1-6}$ alkylene or the like; each of $Y^1$ and $Y^2$ which are independent of each other, is a single bond or the like; R is a $C_{1-20}$ linear, branched or cyclic hydrocarbon group; and a is 0 or 1).

12 Claims, No Drawings

DIAMINE, POLYAMIC ACID, AND POLYIMIDE

TECHNICAL FIELD

The present invention relates to a novel diamine to be a material of a polyimide having an aliphatic secondary amino group in its main chain, and a polyamic acid and a polyimide using it.

BACKGROUND ART

As a polymer produced by using a diamine as a monomer, a condensation polymer such as a polyamide, a polyamic acid, a polyimide, a polyamic acid ester, a polyamide imide or a polyetherimide has been known. Such a condensation polymer has been used as various electronic materials, and it may be used for a wide range of applications, for example, for a liquid crystal alignment film, an optical film, an adhesive film for a semiconductor, an interlayer dielectric film, etc.

It has been known that an excellent liquid crystal alignment film can be obtained from a functional polymer having amino groups introduced to a main chain or side chains of such a condensation polymer. When using such a liquid crystal alignment film, scars on the film surface and peeling of the film which are problematic at the time of so-called rubbing treatment such that the surface of the film is rubbed with a cloth made of e.g. rayon with pressure, can be suppressed, and further, it is possible to prepare a liquid crystal display device which has a high voltage retention, which has a low ion density and which is excellent in the reliability (Patent Document 1).

Further, it has been known that with such a liquid crystal alignment film, a residual image of a photo-alignment type liquid crystal display device can be reduced (Patent Document 2).

Further, it has been known that if highly basic NH groups are present in the skeleton of a functional polymer constituting a liquid crystal alignment film, solubility of such a polymer in a polymer solution decreases, thus leading to gelation and decrease in storage stability. It has been known that such problems can be solved by substituting the NH groups with a thermally-leaving protecting group (Patent Documents 1 and 3).

PRIOR ART DOCUMENTS

Patent Documents

Patent Document 1: WO2010/050523
Patent Document 2: JP-A-2011-076009
Patent Document 3: JP-A-2012-193167

DISCLOSURE OF INVENTION

Technical Problem

It is an object of the present invention to provide a novel diamine to be a material of a polyimide having an aliphatic secondary amino group in its main chain, having such a structure that p-positions of two aminobenzene rings are linked by a group having a moiety in which an aliphatic secondary amine is substituted with a thermally-leaving protecting group, and a polyamic acid and a polyimide using it.

Solution to Problem

The present inventors have conducted extensive studies to achieve the above object and as a result, accomplished the present invention. That is, the present invention provides the following.
1. A diamine represented by the following formula (1):

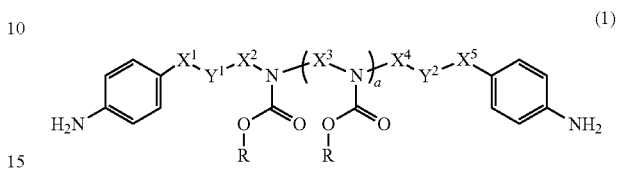

wherein each of $X^1$ and $X^5$ which are independent of each other, is a single bond, —$CH_2$— or —$CH_2CH_2$—, each of $X^2$ and $X^4$ which are independent of each other, is —$CH_2$— or —$CH_2CH_2$—, $X^3$ is a $C_{1-6}$alkylene or cyclohexylene, each of $Y^1$ and $Y^2$ which are independent of each other, is a single bond, —O—, —NH—, —N(CH$_3$)—, —C(=O)—, —C(=O)O—, —C(=O)NH—, —C(=O)N(CH$_3$)—, —OC(=O)—, —NHC(=O)— or —N(CH$_3$)C(=O)—, R is a $C_{1-20}$ linear, branched or cyclic monovalent hydrocarbon group, and a is 0 or 1.
2. The diamine according to the above 1, wherein in the formula (1), each of $X^1$ and $X^5$ which are independent of each other, is a single bond or —$CH_2$—.
3. The diamine according to the above 1 or 2, wherein in the formula (1), each of $X^2$ and $X^4$ which are independent of each other, is —$CH_2$—.
4. The diamine according to any one of the above 1 to 3, wherein in the formula (1), each of $Y^1$ and $Y^2$ which are independent of each other, is a single bond or —O—.
5. The diamine according to any one of the above 1 to 4, wherein in the formula (1), $Y^1$ and $Y^2$ are the same.
6. The diamine according to any one of the above 1 to 5, wherein in the formula (1), a is 0.
7. The diamine according to any one of the above 1 to 6, wherein in the formula (1), R is a t-butyl group or a 9-fluorenylmethyl group.
8. The diamine according to any one of the above 1 to 7, wherein in the formula (1), $Y^1$ and $Y^2$ are a single bond.
9. The diamine according to the above 1, which is represented by the following formula (2), (1-1), (1-6), (1-21), (1-26), (1-33), (1-34), (1-35), (1-36) or (1-38):

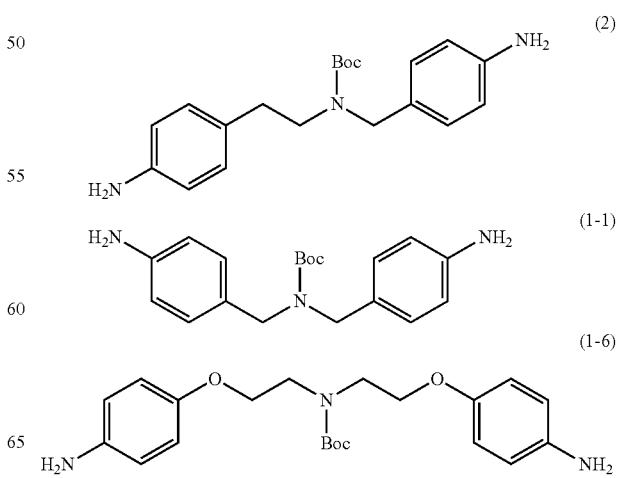

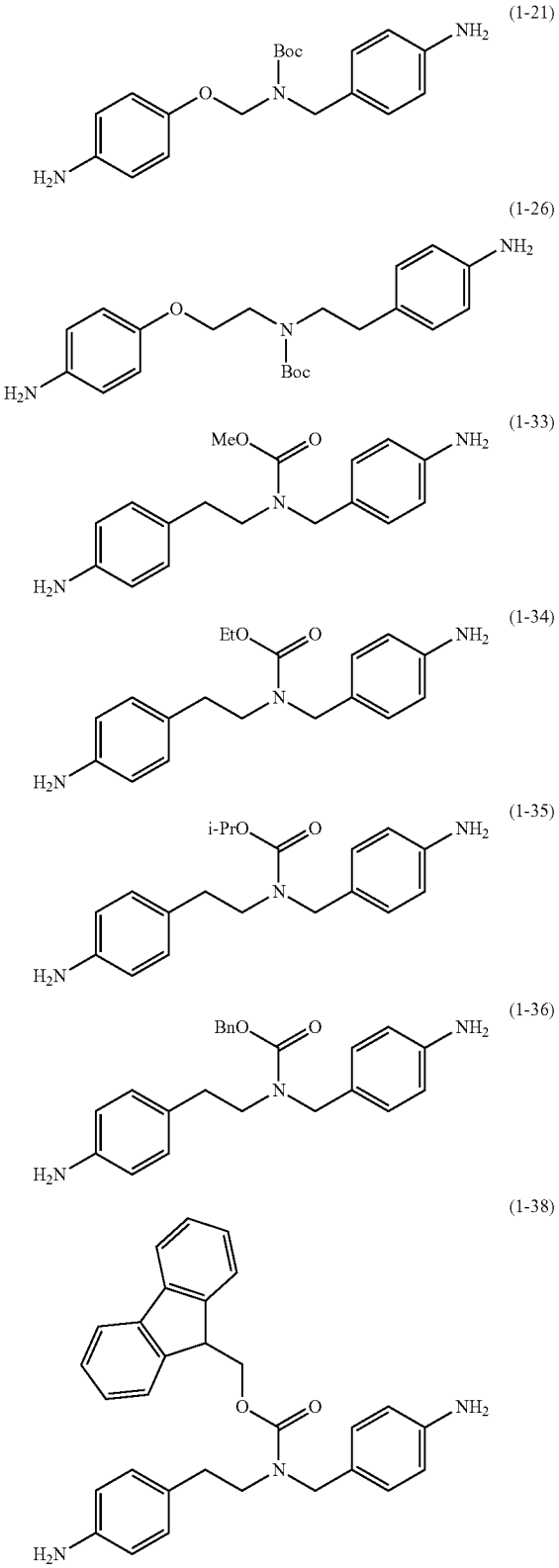

(in the above formulae, Boc represents a tert-butoxycarbonyl group).

10. A polyimide precursor which is obtained by subjecting a diamine component containing the diamine as defined in any one of the above 1 to 9 and a tetracarboxylic acid derivative to polycondensation.

11. The polyimide precursor according to the above 10, wherein the diamine component contains the diamine as defined in any one of the above 1 to 9 in an amount of from 20 to 100 mol %.

12. A polyimide obtained by imidizing the polyimide precursor as defined in the above 10 or 11.

Advantageous Effects of Invention

In a case where the diamine of the present invention and tetracarboxylic acid dianhydride are subjected to polycondensation, since the diamine has a thermally-leaving group, it is possible to obtain a polyimide having an aliphatic secondary amino group in its main chain by heating. Further, the diamine of the present invention undergoes polymerization without gelation with tetracarboxylic acid, and the obtainable polymer will not gelate during storage and is excellent in the stability.

That is, the diamine of the present invention has a thermally-leaving protecting group on the N atom in its main chain, and when it is subjected to polycondensation with tetracarboxylic acid anhydride, salt formation with the formed carboxy group can be suppressed, and accordingly the obtainable polymer will not gelate even during polymerization and during storage. Further, in a case where it is reacted with tetracarboxylic acid diester or tetracarboxylic acid diester dichloride for preparation of a polyamic acid ester, side reactions with the amine in the main chain can be suppressed.

DESCRIPTION OF EMBODIMENTS

Specific Diamine

The diamine of the present invention (hereinafter sometimes referred to as a specific diamine) is represented by the following formula (1):

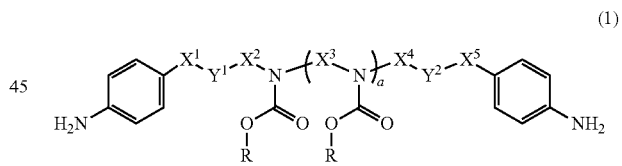

(1)

In the formula (1), each of $X^1$ and $X^5$ which are independent of each other, is a single bond, —$CH_2$— or —$CH_2CH_2$—. Among them, preferred is a single bond or —$CH_2$— from the viewpoint of the alignment property of a liquid crystal alignment film.

In the formula (1), each of $X^2$ and $X^4$ which are independent of each other, is —$CH_2$— or —$CH_2CH_2$—. Among them, preferred is —$CH_2$— in view of the alignment property of a liquid crystal alignment film.

In the formula (1), when $X^1$ and $X^5$ are the same, $X^2$ and $X^4$ are preferably different from each other, and when $X^1$ and $X^5$ are different from each other, $X^2$ and $X^4$ are preferably the same.

In the formula (1), $X^3$ is a $C_{1-4}$ alkylene or cyclohexylene.

In the formula (1), each of $Y^1$ and $Y^2$ which are independent of each other, is a single bond, —O—, —NH—, —N($CH_3$)—, —C(=O)—, —C(=O)O—, —C(=O)NH—, —C(=O)N($CH_3$)—, —OC(=O)—, —NHC (=O)— or —N(CH₃)C(=O)—. Among them, preferred is a single bond, —O—, —C(=O)—, —C(=O)O—, —C(=O)NH—, —C(=O)N(CH₃)—, —OC(=O)—, —NHC(=O)— or —N(CH₃)C(=O)—, from the viewpoint of the solubility of a polymer in preparation of a polyamic acid. Considering the alignment property of a liquid crystal alignment film, more preferred is a single bond or —O—.

In the formula (1), $Y^1$ and $Y^2$ are preferably symmetrical, particularly preferably they are a single bond.

In the formula (1), in a case where $Y^1$ and $Y^2$ are a —NH— group, at the time of polymerization with tetracarboxylic acid dianhydride, the polymer solution may gelate, and in such a case, the —NH— groups are preferably substituted with a thermally-leaving protecting group.

In the formula (1), R is a $C_{1-20}$ linear, branched or cyclic monovalent hydrocarbon group. From the viewpoint of availability, a methyl group, an ethyl group, a n-propyl group, an i-propyl group, a n-butyl group, an i-butyl group, a t-butyl group, a benzyl group, a n-hexadecyl group or a 9-fluorenylmethyl group may be mentioned. Such a substituent may be formed by a conventional organic synthetic means, and from the viewpoint of easiness of preparation, preferred is a methyl group, an ethyl group, an i-propyl group, a t-butyl group, a benzyl group or a 9-fluorenylmethyl group, more preferred is a t-butyl group or a 9-fluorenylmethyl group, and considering solubility of the resulting polymer and thermally leaving property, particularly preferred is a t-butyl group.

In the formula (1), a is 0 or 1. From the viewpoint of easiness of preparation, a is preferably 0.

As specific examples of the formula (1), the following formulae (1-1) to (1-44) and (2) may be mentioned.

(1-1)

(2)

(1-2)

(1-3)

(1-4)
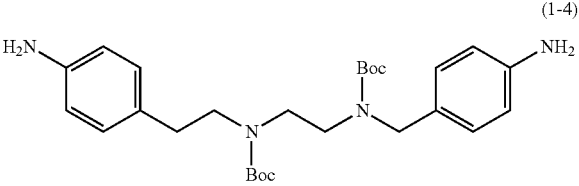

(1-5)
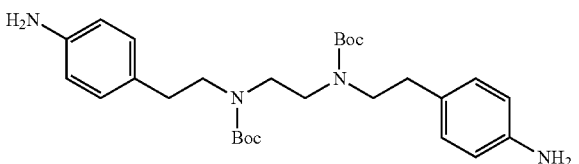

(1-6)
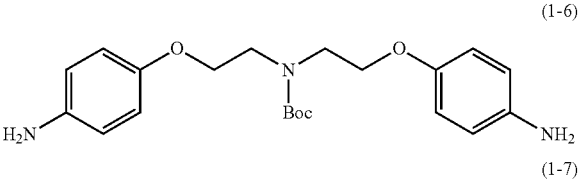

(1-7)
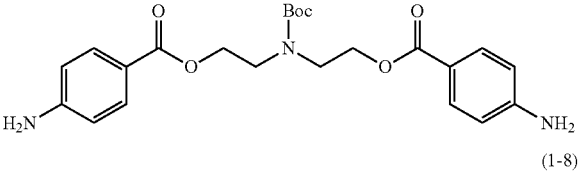

(1-8)
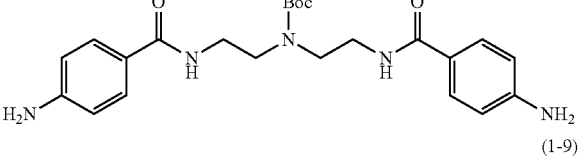

(1-9)
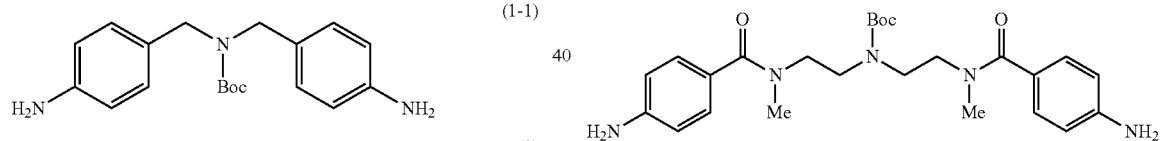

(1-10)
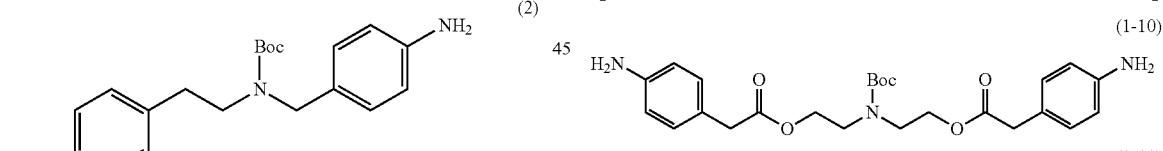

(1-11)
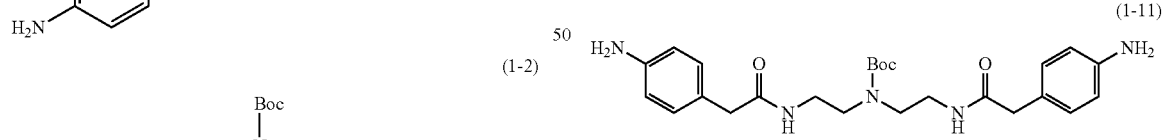

(1-12)
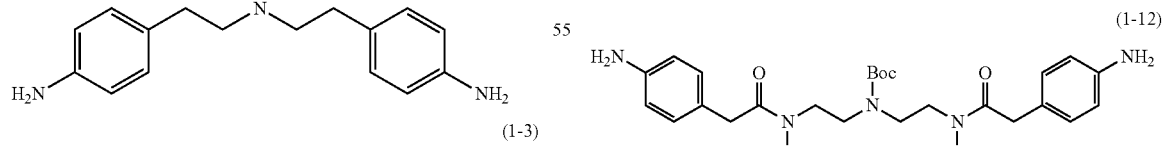

(1-13)
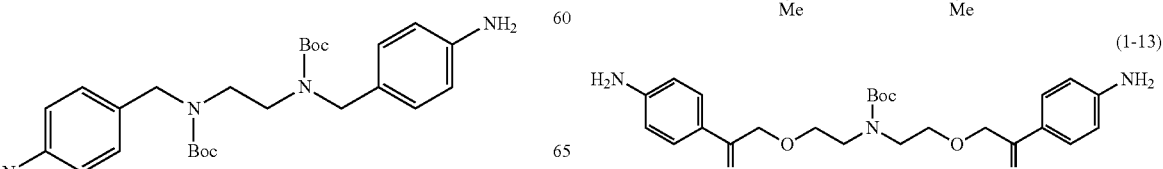

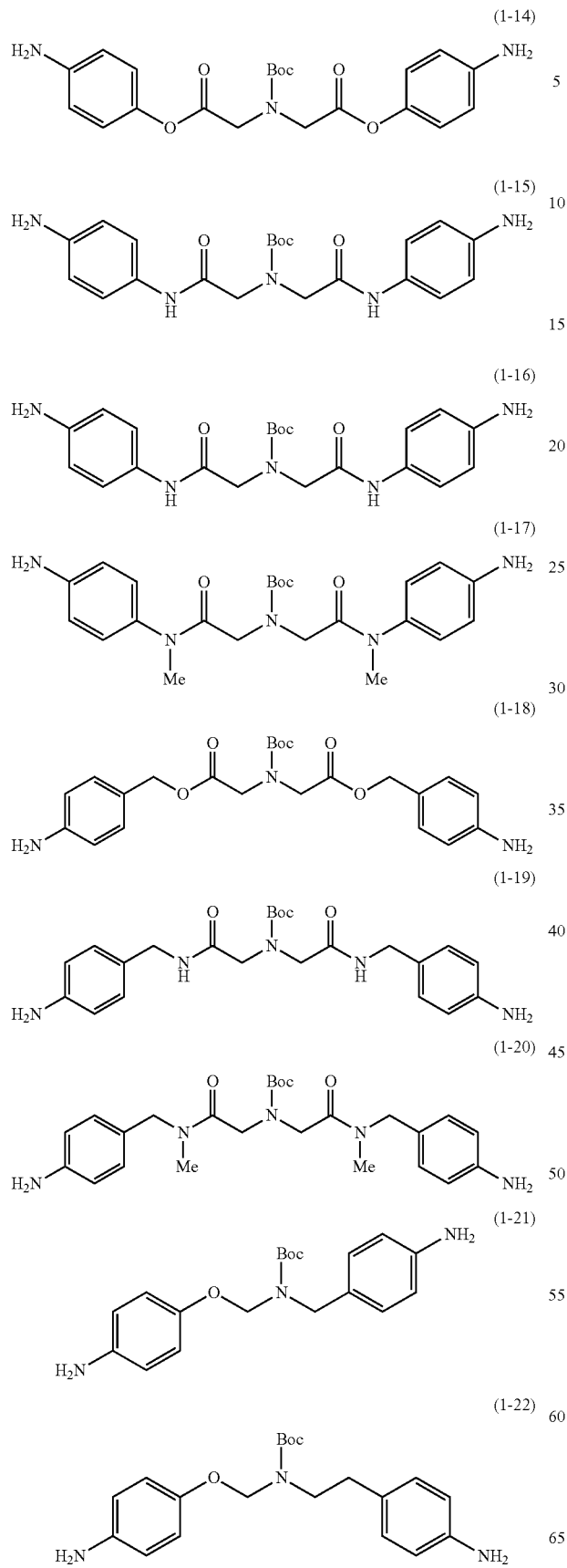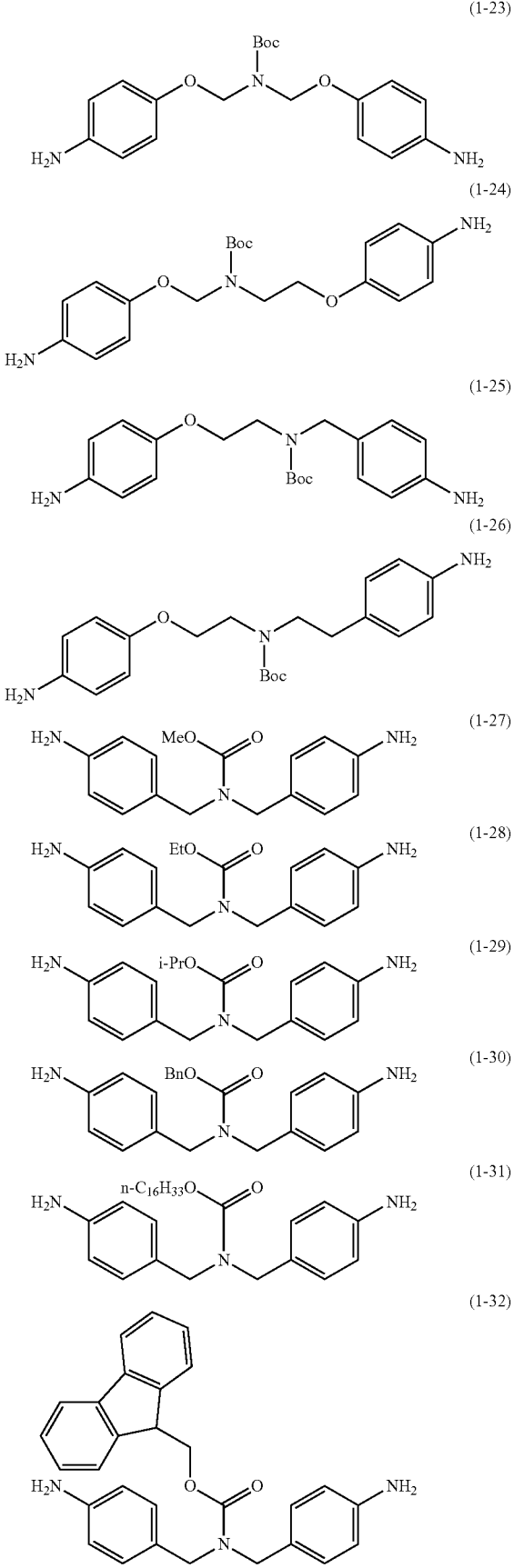

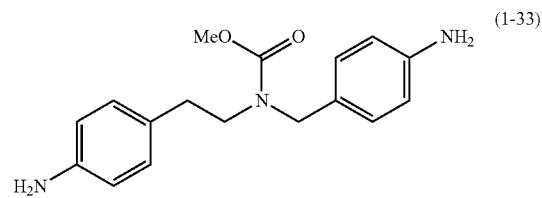
(1-33)

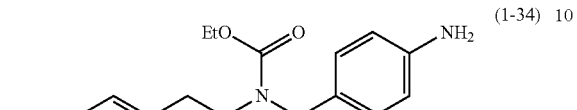
(1-34)

(1-35)

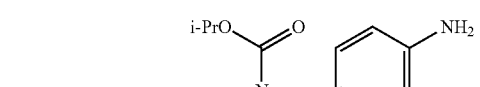
(1-36)

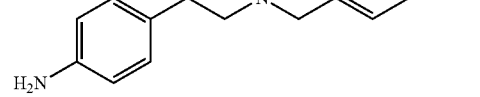
(1-37)

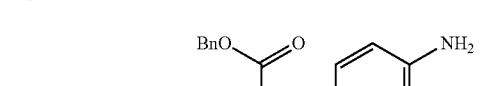
(1-38)

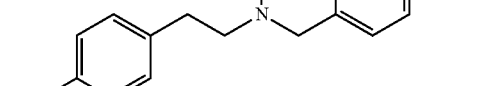
(1-39)

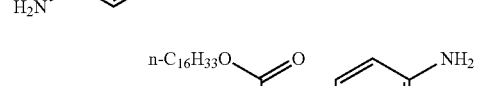
(1-40)

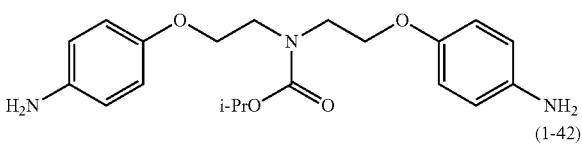
(1-41)

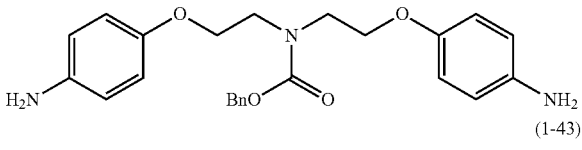
(1-42)

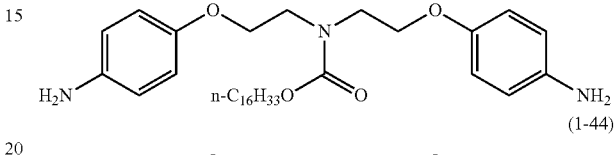
(1-43)

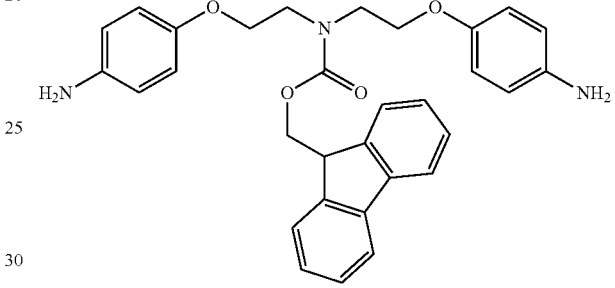
(1-44)

In the formulae (1-1) to (1-44) and (2), Me represents a methyl group, Et an ethyl group, i-Pr an i-propyl group, Bn a benzyl group, and Boc a tert-butoxycarbonyl group.

Among them, preferred is a compound represented by a formula selected from the formulae (1-1) to (1-26), (2), (1-32), (1-38) and (1-44) in which the thermally-leaving group is a t-butyloxycarbonyl group or a 9-fluorenylmethyl group, and more preferred is a compound represented by a formula selected from the formulae (1-1) to (1-26) and (2) in which the thermally-leaving group is a t-butyloxycarbonyl group.

[Method for Preparing Specific Diamine]

The method for preparing the specific diamine of the present invention is not particularly limited. For example, a method of preparing a dinitro compound represented by the following formula (3) and reducing the nitro groups into amino groups in a solvent may be mentioned.

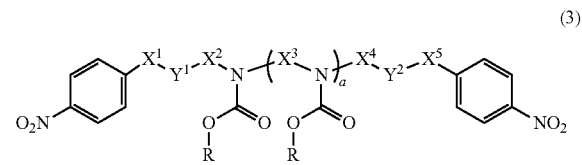
(3)

wherein $X^1$, $X^2$, $X^3$, $X^4$, $X^5$, $Y^1$, $Y^2$, R and a are as defined for the above formula (1).

The method for reducing nitro groups is not particularly limited. For example, reduction is conducted with a hydrogen gas, hydrazine, hydrogen chloride, ammonium chloride or the like using as a catalyst palladium-carbon, platinum oxide, Raney-nickel, platinum-carbon, rhodium-alumina, sulfide of platinum carbon, reduced iron, iron chloride, tin, tin chloride, zinc or the like.

As the solvent, a solvent which has no influence over the reaction may be used. Such a solvent may, for example, be an ester solvent such as ethyl acetate or methyl acetate, an aromatic hydrocarbon solvent such as toluene or xylene, an aliphatic hydrocarbon solvent such as n-hexane, n-heptane or cyclohexane, an ether solvent such as 1,2-dimethoxyethane, tetrahydrofuran or dioxane, an alcohol solvent such as methanol or ethanol, a ketone solvent such as 2-butanone or 4-methyl-2-pentanone, an aprotic polar solvent such as N,N-dimethylformamide, N,N-dimethylacetamide, N-methyl-2-pyrrolidone or dimethyl sulfoxide, or water. Such solvents may be used alone or as a mixture of two or more.

The reaction may be carried out at a reaction temperature under which the reaction will efficiently proceed, so long as the raw material or the product will not decompose, within a range of at most the boiling point of the solvent to be used. Specifically, the reaction temperature is preferably from −78° C. to the boiling point of the solvent, more preferably from 0° C. to the boiling point of the solvent, from the viewpoint of easiness of preparation.

Considering the stability of the NC(=O)OR group in the formula (3), the reaction is preferably carried out under neutral conditions, and the reaction is preferably carried out with a hydrogen gas using as a catalyst palladium-carbon, platinum oxide, Raney-nickel, platinum black, rhodium-alumina or sulfide of platinum carbon.

Further, in a case where $X^1$ in the formula (3) is —CH$_2$— and $Y^1$ is —O—, —NH—, —N(CH$_3$)—, —OC(=O)—, —NHC(=O)— or —N(CH$_3$)C(=O)—, in a case where $X^5$ is —CH$_2$— and $Y^2$ is —O—, —NH—, —N(CH$_3$)—, —OC(=O)—, —NHC(=O)— or —N(CH$_3$)C(=O)—, in a case where $X^1$ and $Y^1$ are a single bond and $X^2$ is —CH$_2$—, and in a case where $X^5$ and $Y^2$ are a single bond and $X^4$ is —CH$_2$—, a reduction method by which the benzyl group in the formula (3) will not be cleaved may be employed.

The reduction method is not limited so long as the benzyl group will not be cleaved. The reduction may be carried out, for example, with a hydrogen gas, hydrazine, hydrogen chloride, ammonium chloride or the like using as a catalyst platinum black, rhodium-alumina, sulfide of platinum carbon, reduced iron, iron chloride, tin, tin chloride, zinc or the like.

Further, as a method for preparing the compound of the formula (3), for example, a method of preparing a dinitro compound represented by the following formula (4), protecting H on the NH group with a protecting group, and reducing the nitro groups into amino groups in a solvent, may be mentioned.

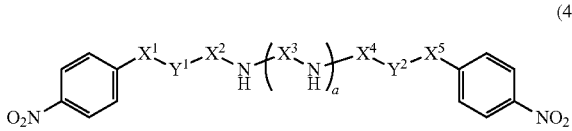

(4)

In the formula (4), $X^1$, $X^2$, $X^3$, $X^4$, $X^5$, $Y^1$, $Y^2$ and a are as defined for the above formula (1).

The method for protecting H on the NH group with a protecting group is not particularly limited. For example, a method of reacting an alkyl chloroformate represented by the following formula (5) or a dialkyl dicarbonate represented by the following formula (6) under neutral conditions or alkaline conditions in a solvent may be mentioned.

(5)

In the formula (5), R is as defined for the above formula (1).

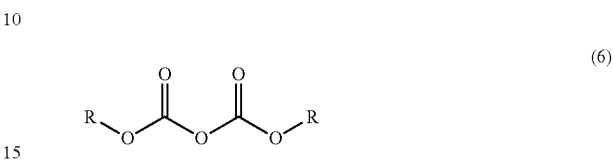

(6)

In the formula (6), R is as defined for the above formula (1).

The solvent and the reaction temperature are in accordance with the above, however, an alcohol solvent and water, which may react with the raw material, are not preferred.

The alkyl chloroformate may, for example, be methyl chloroformate, ethyl chloroformate, n-propyl chloroformate, i-propyl chloroformate, n-butyl chloroformate, i-butyl chloroformate, t-butyl chloroformate, benzyl chloroformate, n-hexadecyl chloroformate or 9-fluorenylmethyl chloroformate, and is preferably methyl chloroformate, ethyl chloroformate, i-propyl chloroformate, benzyl chloroformate, 9-fluorenylmethyl chloroformate or the like.

The dialkyl dicarbonate may, for example, be dimethyl dicarbonate, diethyl dicarbonate, di-t-butyl dicarbonate or dibenzyl dicarbonate, and is preferably diethyl dicarbonate or di-t-butyl dicarbonate.

The method for preparing the compound represented by the formula (4) is not particularly limited, and in a case where $Y^1$ and $Y^2$ are the same, for example, the following method may be mentioned.

For example, in a case where $Y^1$ and $Y^2$ in the formula (4) are a single bond and a is 1, a method of reacting a diamine represented by the following formula (7) and a corresponding 4-nitrophenyl group-substituted aldehyde in a reaction solvent, and then hydrogenating the formed imine bond may, for example, be mentioned. The reaction solvent and the reaction temperature are in accordance with the above, however, water, which may hydrolyze the formed product, is not preferred.

In the above preparation method, in a case where $X^1$ and $X^5$ in the formula (4) are the same and $X^2$ and $X^4$ are the same, a method of reacting one molecule of the amine represented by the formula (7) and two molecules of the 4-nitrophenyl group-substituted aldehyde, and hydrogenating the formed imine may be mentioned.

On the other hand, in a case where $X^1$ and $X^5$ are different from each other, or in a case where $X^2$ and $X^4$ are different from each other, a method of reacting one molecule of the amine represented by the formula (7) and one molecule of the 4-nitrophenyl group-substituted aldehyde, then reacting one more molecule of the 4-nitrophenyl group-substituted aldehyde, and further hydrogenating the formed imine may be mentioned.

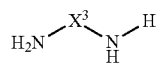

(7)

In the formula (7), $X^3$ is as defined for the above formula (1).

The compound represented by the formula (7) may, for example, be specifically ethylenediamine, 1,3-propanediamine, 1,4-butanediamine, 1,5-pentanediamine, 1,6-hexanediamine or trans-1,4-cyclohexanediamine, and is preferably ethylenediamine.

The 4-nitrophenyl group-substituted aldehyde may, for example, be 4-nitrobenzaldehyde, 4-nitrophenylacetaldehyde, 3-(4-nitrophenyl)propanal or 4-(4-nitrophenyl)butanal, preferably 4-nitrobenzaldehyde.

In a case where $Y^1$ and $Y^2$ in the formula (4) are a single bond and a is 1, as another method for preparing such a compound represented by the formula (4), a method of reacting the amine represented by the formula (7) and a corresponding 4-nitrophenylalkyl halide or sulfonic acid 4-nitrophenylalkyl ester in the presence of an alkali in a reaction solvent may be mentioned. The reaction solvent and the reaction temperature are in accordance with the above. However, a protic solvent such as an alcohol solvent or water may be used so long as it does not react with the raw material.

The 4-nitrophenylalkyl halide may, for example, be 4-nitrobenzyl chloride, 4-nitrophenethyl chloride, 3-(4-nitrophenyl)-1-chloropropane, 4-(4-nitrophenyl)-1-chlorobutane, 4-nitrobenzyl bromide, 4-nitrophenethyl bromide, 3-(4-nitrophenyl)-1-bromopropane, 4-(4-nitrophenyl)-1-bromobutane, 4-nitrobenzyl iodide, 4-nitrophenethyl iodide, 3-(4-nitrophenyl)-1-iodopropane or 4-(4-nitrophenyl)-1-iodobutane.

The sulfonic acid 4-nitrophenylalkyl ester may be available e.g. by a method of reacting a corresponding 4-nitrophenyl alcohol and sulfonyl chloride in the presence of an alkali in a reaction solvent. The reaction solvent and the reaction temperature are in accordance with the above. However, a protic solvent such as an alcohol solvent or water may be used so long as it does not react with the raw material.

The 4-nitrophenyl alcohol may, for example, be 4-nitrobenzyl alcohol, 4-nitrophenethyl alcohol, 3-(4-nitrophenyl)-1-propanol or 4-(4-nitrophenyl)-1-butanol.

The sulfonyl chloride may, for example, be methanesulfonyl chloride, benzenesulfonyl chloride or toluenesulfonyl chloride.

In a case where $Y^1$ and $Y^2$ in the formula (4) are a single bond and a is 0, as a method for preparing such a compound represented by the formula (4), a method of reacting a corresponding 4-nitrophenylalkylamine and 4-nitrophenyl group-substituted aldehyde in a reaction solvent, and hydrogenating the formed imine may, for example, be mentioned. The reaction solvent and the reaction temperature are in accordance with the above, however, water, which may hydrolyze the formed product, is not preferred.

The 4-nitrophenylalkylamine may, for example, be 4-nitrobenzylamine, 4-nitrophenethylamine, 3-(4-nitrophenyl)-1-propylamine or 4-(4-nitrophenyl)-1-butylamine.

In a case where $Y^1$ and $Y^2$ in the formula (4) are a single bond and a is 0, as another method for preparing such a compound represented by the formula (4), a method of reacting a corresponding 4-nitrophenylalkylamine and 4-nitrophenylalkyl halide in the presence of an alkali in a reaction solvent may, for example, mentioned. The reaction solvent and the reaction temperature are in accordance with the above. However, a protic solvent such as an alcohol solvent or water may be used so long as it does not react with the raw material.

Further, as another method for preparing the compound represented by the formula (3), in a case where $Y^1$ and $Y^2$ are a single bond and a is 1, a method of reacting the diamine represented by the formula (7) and the alkyl chloroformate represented by the formula (5) or the dialkyl dicarbonate represented by the formula (6) under neutral conditions or in the presence of an alkali, in a reaction solvent, substituting H on the NH group with a —C(=O)OR, and reacting the corresponding 4-nitrophenylalkyl halide or sulfonic acid 4-nitrophenylalkyl ester in the presence of an alkali in a reaction solvent may, for example, be mentioned. The reaction solvent and the reaction temperature are in accordance with the above. However, a protic solvent such as an alcohol solvent or water may be used so long as it does not react with the raw material.

In the above preparation method, in a case where $X^1$ and $X^5$ in the formula (3) are the same and $X^2$ and $X^4$ are the same, the method of reacting one molecule of the diamine represented by the formula (7) and two molecules of the 4-nitrophenylalkyl halide or sulfonic acid 4-nitrophenylalkyl ester all at once, may be mentioned.

On the other hand, in a case where $X^1$ and $X^5$ in the formula (3) are different from each other, or in a case where $X^2$ and $X^4$ are different from each other, a method of reacting one molecule of the diamine represented by the formula (7) and one molecule of the 4-nitrophenylalkyl halide or sulfonic acid 4-nitrophenylalkyl ester and then reacting one more molecule of the 4-nitrophenylalkyl halide or sulfonic acid 4-nitrophenylalkyl ester may, for example, be mentioned.

Each of $Y^1$ and $Y^2$ in the formula (3) is, in a case where it is not a single bond, a linking group selected from the group consisting of —O—, —NH—, —N(CH$_3$)—, —C(=O)—, —C(=O)O—, —C(=O)NH—, —C(=O)N(CH$_3$)—, —OC(=O)—, —NHC(=O)— and —N(CH$_3$)C(=O)—, and such a linking group may be formed by a conventional synthetic organic chemical means.

For example, in a case where $Y^1$ and $Y^2$ in the formula (3) is —O—, a method of reacting a corresponding 4-nitrophenyl group-substituted halide or 4-nitrophenyl group-substituted sulfonic acid ester and an alcohol represented by following formula (8) in the presence of an alkali in a reaction solvent, or a method of reacting a corresponding hydroxy group-substituted 4-nitrobenzene derivative and a halide represented by the formula (9) or sulfonic acid ester in the presence of an alkali in a reaction solvent may be mentioned. The reaction solvent and the reaction temperature are in accordance with the above. However, a protic solvent such as an alcohol solvent or water may be used so long as it does not react with the raw material.

The 4-nitrophenyl group-substituted halide may, for example, be 4-nitrofluorobenzene, 4-nitrochlorobenzene, 4-nitrobenzyl chloride, 4-nitrophenethyl chloride, 4-nitrobenzyl bromide, 4-nitrophenethyl bromide, 4-nitrobenzyl iodide or 4-nitrophenethyl iodide.

The hydroxy group-substituted 4-nitrobenzene derivative may, for example, be 4-nitrophenol, 4-nitrobenzyl alcohol or 4-nitrophenethyl alcohol.

The 4-nitrophenyl group-substituted sulfonic acid ester may, for example, be 4-nitrophenyl methanesulfonate, 4-nitrobenzyl methanesulfonate, 4-nitrophenethyl methanesulfonate, 4-nitrophenyl toluenesulfonate, 4-nitrobenzyl toluenesulfonate or 4-nitrophenethyl toluenesulfonate.

In the above preparation method, in a case where $X^1$ and $X^5$ in the formula (3) are the same, as a method of preparing such a compound represented by the formula (3), a method of reacting two molecules of the 4-nitrophenyl group-substituted halide or 4-nitrophenyl group-substituted sulfonic acid ester all at once may be mentioned.

On the other hand, in a case where $X^1$ and $X^5$ in the formula (3) are different from each other, as a method for preparing such a compound represented by the formula (3), a method of reacting one molecule of the 4-nitrophenyl group-substituted halide or 4-nitrophenyl group-substituted sulfonic acid ester and then reacting one more molecule of the 4-nitrophenyl group-substituted halide or 4-nitrophenyl group-substituted sulfonic acid ester may be mentioned.

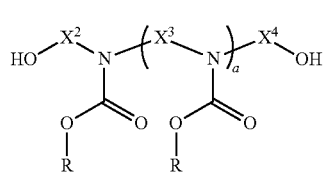

(8)

In the formula (8), $X^2$, $X^3$, $X^4$, R and a are as defined for the above formula (1).

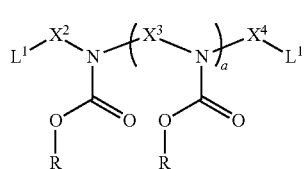

(9)

In the formula (9), $X^2$, $X^3$, $X^4$, R and a are as defined for the above formula (1), and $L^1$ is halogen, an alkanesulfonyloxy group or an arenesulfonyloxy group.

The method for preparing the compound represented by the formula (8) is not particularly limited. For example, a method of reacting the alkyl chloroformate represented by the formula (5) or the dialkyl dicarbonate represented by the formula (6) and a corresponding dihydroxyalkylamine under neutral conditions or in the presence of an alkali, in a reaction solvent may be mentioned. The reaction solvent and the reaction temperature are in accordance with the above. However, a protic solvent such as an alcohol solvent or water may be used so long as it does not react with the raw material.

The dihydroxyalkylamine may, for example, be dimethanolamine, diethanolamine, 2-hydroxymethylaminoethanol, N,N'-bishydroxymethylethylenediamine, N,N'-bishydroxymethyl-1,3-propanediamine, N,N'-bishydroxymethyl-1,4-butanediamine, N,N'-bishydroxymethyl-1,5-pentanediamine, N,N'-bishydroxymethyl-1,6-hexanediamine, N,N'-bishydroxyethylethylenediamine, N,N'-bishydroxyethyl-1,3-propanediamine, N,N'-bishydroxyethyl-1,4-butanediamine, N,N'-bishydroxyethyl-1,5-pentanediamine, N,N'-bishydroxyethyl-1,6-hexanediamine or N,N'-bishydroxyethyl-trans-1,4-cyclohexanediamine.

Further, the dihydroxyalkylamine may also be prepared by hydroxyalkylating a corresponding amine or monohydroxyalkylamine. The hydroxymethylating method is not particularly limited, and a hydroxymethylating method of reacting the amine or the monohydroxyalkylamine and paraformaldehyde or formalin may, for example, be mentioned. The hydroxyethylating method is not particularly limited, and for example, a method of reacting the amine or the monohydroxyalkylamine and a 2-haloethanol under basic conditions, a method of reacting the amine or the monohydroxyalkylamine and ethylene oxide, or a method of reacting the amine or the monohydroxyalkylamine and an α-haloacetic acid ester and then reducing the ester group may be mentioned. The reaction solvent and the reaction temperature in such reactions are in accordance with the above. However, at the time of reducing the ester group, a solvent having a reducing functional group such as an ester solvent or a ketone solvent may be used so long as it has no influence over the reaction.

The amine may be ammonia or the compound represented by the formula (7).

The monohydroxyalkylamine may, for example, be aminomethanol, 2-aminoethanol, N-hydroxymethylethylenediamine, N-hydroxymethyl-1,3-propanediamine, N-hydroxymethyl-1,4-butanediamine, N-(2-hydroxyethyl)ethylenediamine, N-(2-hydroxyethyl)-1,3-propanediamine, N-(2-hydroxyethyl)-1,4-butanediamine, N-(2-hydroxyethyl)-1,5-pentanediamine or N-(2-hydroxyethyl)-1,6-hexanediamine.

The 2-haloethanol may, for example, be 2-chloroethanol or 2-bromoethanol.

The α-haloacetic acid ester may, for example, be methyl chloroacetate, ethyl chloroacetate, methyl bromoacetate, ethyl bromoacetate or t-butyl bromoacetate.

As a method for reducing the ester group, for example, a method of using lithium aluminum hydride may be mentioned. The reaction solvent and the reaction temperature are in accordance with the above. However, a solvent having a reducing functional group such as an ester solvent or a ketone solvent or a protic solvent such as an alcohol solvent or water may be used so long as it does not react with the raw material.

The method for preparing the compound represented by the formula (9) is not particularly limited. For example, a method of converting the hydroxy groups in the compound represented by the formula (8) to a halogen or a sulfonic acid ester may be mentioned.

As a method for converting the hydroxy groups in the formula (8) into a chloro group, a method of reacting the compound represented by the formula (8) and thionyl chloride or phosphoryl chloride, or a method of reacting the compound represented by the formula (8) and carbon tetrachloride in the presence of triphenylphosphine may, for example, be mentioned. The reaction solvent and the reaction temperature are in accordance with the above. However, a protic solvent such as an alcohol solvent or water may be used so long as it does not react with the raw material.

As a method for converting the hydroxy groups in the formula (8) into a bromo group, a method of reacting the compound represented by the formula (8) and hydrogen bromide or phosphorus tribromide, a method of reacting the compound represented by the formula (8) and carbon tetrabromide in the presence of triphenylphosphine, or a method of reacting the compound represented by the formula (8) and N-bromosuccinimide in the presence of triphenylphosphine may, for example, be mentioned. The reaction solvent and the reaction temperature are in accordance with the above. However, a protic solvent such as an alcohol solvent or water may be used so long as it does not react with the raw material.

As a method for converting the hydroxy groups in the formula (8) into an iodo group, a method of reacting the compound represented by the formula (8) and iodine in the presence of triphenylphosphine may, for example, be mentioned. Further, a method of reacting the compound of the formula (9) wherein $L^1$ is a chloro group, a bromo group, an alkanesulfonyloxy group or an arenesulfonyloxy group, and sodium iodide, potassium iodide, tetrabutylammonium iodide or the like may be mentioned. The reaction solvent and the reaction temperature are in accordance with the above. However, a protic solvent such as an alcohol solvent or water may be used so long as it does not react with the raw material.

The method for converting the hydroxy groups in the formula (8) into a sulfonic acid ester, a method of reacting the compound represented by the formula (8) and sulfonyl chloride in the presence of an alkali may be mentioned.

In a case where $Y^1$ and $Y^2$ in the formula (3) are —NH— or —N(CH$_3$)—, a method of reacting a corresponding amino group-substituted 4-nitrobenzene derivative and the halide or sulfonic acid ester represented by the formula (9) in the presence of an alkali in a reaction solvent may, for example, be mentioned.

The reaction solvent and the reaction temperature are in accordance with the above. However, a protic solvent such as an alcohol solvent or water may be used so long as it does not react with the raw material.

In the above preparation method, in a case where $X^1$ and $X^5$ in the formula (3) are the same, as a method for preparing such a compound represented by the formula (3), a method of reacting two molecules of the amino group-substituted 4-nitrobenzene derivative all at once may be mentioned.

On the other hand, in a case where $X^1$ and $X^5$ in the formula (3) are different from each other, as a method for preparing such a compound represented by the formula (3), a method of reacting one molecule of the halide or sulfonic acid ester represented by the formula (9) and one molecule of the amino group-substituted 4-nitrobenzene derivative and then reacting one more molecule of the amino group-substituted 4-nitrobenzene derivative may be mentioned.

The amino group-substituted 4-nitrobenzene derivative may, for example, be 4-nitroaniline, N-methyl-4-nitroaniline, 4-nitrobenzylamine, N-methyl-4-nitrobenzylamine, 4-nitrophenethylamine or N-methyl-4-nitrophenethylamine.

In a case where $Y^1$ and $Y^2$ in the formula (3) are —C(=O)—, a method of reacting a corresponding haloalkylcarbonyl group-substituted 4-nitrobenzene derivative, alkanesulfonyl alkylcarbonyl group-substituted 4-nitrobenzene derivative or arenesulfonyl alkylcarbonyl group-substituted 4-nitrobenzene derivative and the amine compound substituted with a protecting group on the N atom represented by the formula (8) in the presence of an alkali in a reaction solvent may, for example, be mentioned. The reaction solvent and the reaction temperature are in accordance with the above. However, a protic solvent such as an alcohol solvent or water may be used so long as it does not react with the raw material.

In the above preparation method, in a case where $X^1$ and $X^5$ in the formula (3) are the same, as a method for preparing such a compound represented by the formula (3), a method of reacting one molecule of the amine compound substituted with a protecting group on the N atom represented by the formula (8) and two molecules of the haloalkylcarbonyl group-substituted 4-nitrobenzene derivative, alkanesulfonyl alkylcarbonyl group-substituted 4-nitrobenzene derivative or arenesulfonyl alkylcarbonyl group-substituted 4-nitrobenzene derivative all at once may be mentioned.

On the other hand, in a case where $X^1$ and $X^5$ in the formula (3) are different from each other, as a method for preparing such a compound represented by the formula (3), a method of reacting one molecule of the amine compound substituted with a protecting group on the N atom represented by the formula (8) and one molecule of the haloalkylcarbonyl group-substituted 4-nitrobenzene derivative, alkanesulfonyl alkylcarbonyl group-substituted 4-nitrobenzene derivative or arenesulfonyl alkylcarbonyl group-substituted 4-nitrobenzene derivative and then reacting one more molecule of the haloalkylcarbonyl group-substituted 4-nitrobenzene derivative, alkanesulfonyl alkylcarbonyl group-substituted 4-nitrobenzene derivative or arenesulfonyl alkylcarbonyl group-substituted 4-nitrobenzene derivative may be mentioned.

The haloalkylcarbonyl group-substituted 4-nitrobenzene derivative may, for example, be 4-nitrophenyl chloromethyl ketone, 4-nitrophenyl bromomethyl ketone, 4-nitrophenyl iodomethyl ketone, 3-chloro-1-(4-nitrophenyl)-1-propanone, 3-bromo-1-(4-nitrophenyl)-1-propanone, 1-chloro-3-(4-nitrophenyl)-2-propanone or 1-bromo-3-(4-nitrophenyl)-2-propanone.

In a case where $Y^1$ in the formula (3) is —C(=O)O— and $Y^2$ is —OC(=O)—, a method of reacting a corresponding 4-nitrophenyl group-substituted acid halide and the alcohol represented by the formula (8) under neutral conditions or in the presence of an alkali, in a reaction solvent, or a method of reacting a corresponding 4-nitrophenyl group-substituted carboxylic acid and the alcohol represented by the formula (8) in the presence of a dehydration condensation agent in a reaction solvent may, for example, be mentioned. The reaction solvent and the reaction temperature are in accordance with the above. However, a protic solvent such as an alcohol solvent or water may be used so long as it does not react with the raw material.

In the above preparation method, in a case where $X^1$ and $X^5$ in the formula (3) are the same, as a method for preparing such a compound represented by the formula (3), a method of reacting two molecules of 4-nitrophenyl group-substituted acid halide all at once may be mentioned.

On the other hand, in a case where $X^1$ and $X^5$ in the formula (3) are different from each other, as a method for preparing such a compound represented by the formula (3), a method of reacting one molecule of the alcohol represented by the formula (8) and one molecule of the 4-nitrophenyl group-substituted acid halide or a corresponding 4-nitrophenyl group-substituted carboxylic acid and then reacting one more molecule of the 4-nitrophenyl group-substituted acid halide or a corresponding 4-nitrophenyl group-substituted carboxylic acid may be mentioned.

The 4-nitrophenyl group-substituted acid halide may, for example, be 4-nitrobenzoic acid chloride, 4-nitrophenyl acetic acid chloride or 4-nitrophenyl propionic acid chloride.

The 4-nitrophenyl group-substituted carboxylic acid may, for example, be 4-nitrobenzoic acid, 4-nitrophenylacetic acid or 4-nitrophenylpropionic acid.

The dehydration condensation agent may, for example, be dicyclohexylcarbodiimide, 1-ethyl-3-(3-dimethylaminopropyl)carbodiimide hydrochloride, diisopropylcarbodiimide, 1,1'-carbonyldiimidazol, bis(2-oxo-3-oxazolidinyl)phosphine hydrochloride, di-2-pyridyl carbonate, triphenyl phosphite, dimethoxy-1,3,5-triazinylmethyl morpholinium, O-(benzotriazol-1-yl)-N,N,N',N'-tetramethyluronium tetrafluoroborate, O-(benzotriazol-1-yl)-N,N,N',N'-tetramethyluronium hexafluorophosphate or diphenyl(2,3-dihydro-2-thioxo-3-benzoxazolyl)phosphonate.

In a case where $Y^1$ in the formula (3) is —C(=O)NH— or —C(=O)N(NH$_3$)— and $Y^2$ is —NHC(=O) or —NH(CH$_3$)C(=O), a method of reacting a corresponding 4-nitrophenyl group-substituted amide and the halide or sulfonic acid ester represented by the formula (9) in the presence of an alkali in a reaction solvent may, for example, be mentioned. The reaction solvent and the reaction temperature are in accordance with the above. However, a protic solvent such as an alcohol solvent or water may be used so long as it does not react with the raw material.

In the above preparation method, in a case where $X^1$ and $X^5$ in the formula (3) are the same, as a method for preparing such a compound represented by the formula (3), a method of reacting one molecule of the halide or sulfonic acid ester represented by the formula (9) and two molecules of the 4-nitrophenyl group-substituted amide all at once may be mentioned.

On the other hand, in a case where $X^1$ and $X^5$ in the formula (3) are different from each other, as a method for preparing such a compound represented by the formula (3), a method of reacting one molecule of the halide or sulfonic acid ester represented by the formula (9) and one molecule of the 4-nitrophenyl group-substituted amide and then reacting one more molecule of the 4-nitrophenyl group-substituted amide may be mentioned.

The 4-nitrophenyl group-substituted amide may, for example, be 4-nitrobenzamide, N-methyl-4-nitrobenzamide, 4-nitrophenylacetylamide, N-methyl-4-nitrophenylacetylamide or 4-nitrophenylpropionamide.

Further, such a compound may also be prepared by reacting the 4-nitrophenyl group-substituted acid halide and ammonia or methylamine in a reaction solvent. The reaction solvent and the reaction temperature are in accordance with the above. However, a protic solvent such as an alcohol solvent or water may be used so long as it does not react with the raw material.

In a case where $Y^1$ in the formula (3) is —OC(=O)— and $Y^2$ is —C(=O)O, a method of reacting a corresponding hydroxy group-substituted 4-nitrobenzene derivative and a compound represented by the following formula (10) in the presence of a dehydration condensation agent, or a method of reacting a corresponding hydroxy group-substituted 4-nitrobenzene derivative and a compound represented by the following formula (11) under neutral conditions or in the presence of an alkali may, for example, be mentioned.

The reaction solvent and the reaction temperature are in accordance with the above. However, a protic solvent such as an alcohol solvent or water may be used so long as it does not react with the raw material.

In the above preparation method, in a case where $X^1$ and $X^5$ in the formula (3) are the same, as a method for preparing such a compound represented by the formula (3), a method of reacting two molecules of the hydroxy group-substituted 4-nitrobenzene derivative all at once may be mentioned.

On the other hand, in a case where $X^1$ and $X^5$ in the formula (3) are different from each other, as a method for preparing such a compound represented by the formula (3), a method of reacting one molecule of the compound represented by the following formula (10) or the compound represented by the following formula (11) and one molecule of the hydroxy group-substituted 4-nitrobenzene derivative and then reacting one more molecule of the hydroxy group-substituted 4-nitrobenzene derivative may be mentioned.

In a case where $Y^1$ in the formula (3) is —OC(=O)— and $Y^2$ is —C(=O)O—, as another method for preparing such a compound represented by the formula (3), a method of reacting the 4-nitrophenyl group-substituted halide or 4-nitrophenyl group-substituted sulfonic acid ester and the compound represented by the formula (10) in the presence of an alkali may, for example, be mentioned. The reaction solvent and the reaction temperature are in accordance with the above. However, a protic solvent such as an alcohol solvent or water may be used so long as it does not react with the raw material.

In the above preparation method, in a case where $X^1$ and $X^5$ in the formula (3) are the same, as another method for preparing such a compound represented by the formula (3), a method of reacting two molecules of the 4-nitrophenyl group-substituted halide or 4-nitrophenyl group-substituted sulfonic acid ester all at once may be mentioned.

On the other hand, in a case where $X^1$ and $X^5$ in the formula (3) are different from each other, as a method for preparing such a compound represented by the formula (3), a method of reacting one molecule of the compound represented by the following formula (10) and one molecule of the 4-nitrophenyl group-substituted halide or 4-nitrophenyl group-substituted sulfonic acid ester and then reacting one more molecule of the 4-nitrophenyl group-substituted halide or 4-nitrophenyl group-substituted sulfonic acid ester may be mentioned.

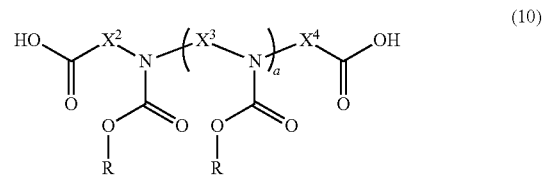

(10)

In the formula (10), $X^2$, $X^3$, $X^4$, R and a are as defined for the above formula (1).

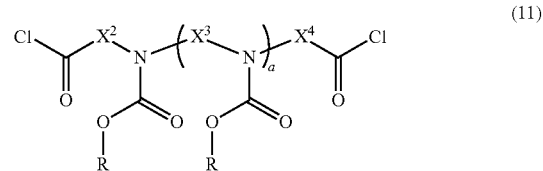

(11)

In the formula (11), $X^2$, $X^3$, $X^4$, R and a are as defined for the above formula (1).

The method for preparing the compound represented by the formula (10) is not particularly limited. For example, a method of reacting a corresponding amine dicarboxylic acid and the alkyl chloroformate represented by the formula (5) or the dialkyl dicarbonate represented by the formula (6) under neutral conditions or in the presence of an alkali, in a reaction solvent may be mentioned. The reaction solvent and the reaction temperature are in accordance with the above. However, a protic solvent such as an alcohol solvent or water may be used so long as it does not react with the raw material.

The amine dicarboxylic acid may, for example, be iminodiacetic acid, N-carboxymethyl-β-alanine, N-carboxyethyl-β-alanine, ethylenediamine-N,N'-diacetic acid, N,N'-1,2-ethanediyl-bis-β-alanine, 1,3-propanediamine-N,N'-diacetic acid, N,N'-1,3-propanediyl-bis-β-alanine, 1,4-butanediamine-N,N'-diacetic acid, N,N'-1,4-butanediyl-bis-β-alanine, 1,5-pentanediamine-N,N'-diacetic acid or 1,6-hexanediamine-N,N'-diacetic acid.

Further, the amine dicarboxylic acid may also be prepared by carboxyalkylating an amine or an amine monocarboxylic acid.

As a method for carboxyalkylating an amine or an amine monocarboxylic acid, a method of reacting the amine or the amine monocarboxylic acid and a corresponding halogen-substituted carboxylic acid or a method of reacting the amine or the amine monocarboxylic acid and acrylic acid may, for example, be mentioned. The reaction solvent and the reaction temperature are in accordance with the above. However, a protic solvent such as an alcohol solvent or water may be used so long as it does not react with the raw material.

The amine monocarboxylic acid may, for example, be glycine, β-alanine, N-(2-aminoethyl)glycine, N-(3-aminopropyl)glycine, N-(4-aminobutyl)glycine, N-(5-aminopentyl)glycine, N-(6-aminohexyl)glycine, N-(2-aminoethyl) 1-alanine, N-(3-aminopropyl) β-alanine, N-(4-aminobutyl) p-alanine or N-(6-aminohexyl) 1-alanine.

The halogen-substituted carboxylic acid may, for example, be chloroacetic acid, bromoacetic acid, 3-chloropropionic acid or 3-bromopropionic acid.

Further, the amine dicarboxylic acid may also be prepared by alkoxycarbonyl-alkylating the amine, the amine monocarboxylic acid or an amine monocarboxylic acid ester, followed by hydrolysis with an acid or an alkali.

As a method for alkoxycarbonyl-alkylating the amine, the amine monocarboxylic acid or the amine monocarboxylic acid ester, a method of reacting the amine or the amine monocarboxylic acid and a corresponding halogen-substituted carboxylic acid ester or a method of reacting the amine or the amine monocarboxylic acid and an acrylic acid ester may, for example, be mentioned. The reaction solvent and the reaction temperature are in accordance with the above. However, a protic solvent such as an alcohol solvent or water may be used so long as it does not react with the raw material.

The halogen-substituted carboxylic acid ester may, for example, be methyl chloroacetate, ethyl chloroacetate, methyl bromoacetate, ethyl bromoacetate, methyl 3-chloropropionate, ethyl 3-chloropropionate, methyl 3-bromopropionate or ethyl 3-bromopropionate.

The acrylic acid ester may, for example, be methyl acrylate or ethyl acrylate.

The method for preparing the compound represented by the formula (11) is not particularly limited. For example, the compound represented by the formula (11) may be prepared by reacting the compound represented by the formula (10) and thionyl chloride or oxalyl chloride. The reaction solvent and the reaction temperature are in accordance with the above. However, a protic solvent such as an alcohol solvent or water may be prepared so long as it does not react with the raw material.

In a case where $Y^1$ in the formula (3) is —NHC(=O)— or —N(CH$_3$)C(=O)— and $Y^2$ is —C(=O)NH or —C(=O)N(CH$_3$), a method of reacting a corresponding amine group-substituted 4-nitrobenzene derivative and the compound represented by the formula (10) in the presence of a dehydration condensation agent in a reaction solvent, or a method of reacting a corresponding amino group-substituted 4-nitrobenzene derivative and the compound represented by the formula (11) under neutral conditions or in the presence of an alkali, in a reaction solvent may, for example, be mentioned. The reaction solvent and the reaction temperature are in accordance with the above. However, a protic solvent such as an alcohol solvent or water may be used so long as it does not react with the raw material.

In the above preparation method, in a case where $X^1$ and $X^5$ in the formula (3) are the same, as a method for preparing such a compound represented by the formula (3), a method of reacting one molecule of the compound represented by the formula (10) or the compound represented by the formula (11) and two molecules of the amino group-substituted 4-nitrobenzene derivative all at once may be mentioned.

On the other hand, in a case where $X^1$ and $X^5$ in the formula (3) are different from each other, as a method for preparing such a compound represented by the formula (3), a method of reacting one molecule of the compound represented by the following formula (10) or the compound represented by the following formula (11) and one molecule of the amino group-substituted 4-nitrobenzene derivative and then reacting one more molecule of the amino group-substituted 4-nitrobenzene derivate may be mentioned.

In a case where $Y^1$ and $Y^2$ in the formula (1) are a single bond, as another method for preparing the specific diamine, for example, a method for preparing a diamine represented by the following formula (12) and substituting H on the NH group with a protecting group may be mentioned.

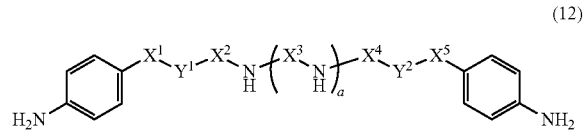

(12)

In the formula (25), $X^1$, $X^2$, $X^3$, $X^4$, $X^5$, $Y^1$, $Y^2$ and a are as defined for the above formula (1).

The method for substituting H on the NH group with a protecting group is not particularly limited. For example, a method of reacting the diamine of the formula (12) and the alkyl chloroformate represented by the formula (5) or the dialkyl dicarbonate represented by the formula (6) under neutral conditions or under alkaline conditions in a reaction solvent may be mentioned.

The reaction solvent and the reaction temperature are in accordance with the above. However, a protic solvent such as an alcohol solvent or water may be used so long as it does not react with the raw material.

As a method for preparing the compound represented by the formula (12), in a case where a in the formula (12) is 0, a method of reacting a corresponding 4-nitrophenyl alkylamine and 4-nitrophenyl group-substituted aldehyde and then reducing the nitro group and the imide bond in the formed nitrophenyl group-substituted imine compound all at once in a hydrogen atmosphere in a reaction solvent, may be mentioned. The reaction solvent and the reaction temperature are in accordance with the above. However, water, which may hydrolyze the imine bond, is not preferred.

In a case where a in the formula (12) is 1, a method of reacting the corresponding compound represented by the formula (7) and 4-nitrophenyl group-substituted aldehyde, and reducing the nitro group and the imine bond in the formed nitrophenyl group-substituted imine compound all at once in a nitrogen atmosphere in a reaction solvent may be mentioned.

The reducing method is not particularly limited, and for example, reduction may be conducted with a hydrogen gas using as a catalyst palladium-carbon, platinum oxide, Raney-nickel, platinum-carbon, rhodium-alumina, sulfide of platinum carbon or the like.

The reaction solvent and the reaction temperature are as defined above. However, water, which may hydrolyze the imine bond, is not preferred.

On the other hand, in a case where $Y^1$ and $Y^2$ are not symmetrical, the method for preparing the compound represented by the formula (4) is properly selected depending upon the structure of the aimed compound, utilizing e.g. the method for forming a linking group employed when $Y^1$ and $Y^2$ are the same.

For example, in a case where $Y^1$ is —O—, $Y^2$ is a single bond and a is 0, for preparation of such a compound represented by the formula (4), a method of reacting a corresponding compound represented by the following formula (13) and a 4-nitrophenylalkylamine in the presence of an alkali in a reaction solvent may, for example, be mentioned. The reaction solvent and the reaction temperature are in accordance with the above. However, a protic solvent such as an alcohol solvent or water may be used so long as it does not react with the raw material.

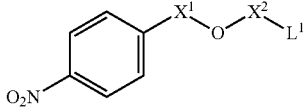

(13)

In the formula (13), $X^1$ and $X^2$ are as defined for the above formula (1), and $L^1$ is as defined for the above formula (9).

The compound represented by the formula (13) may, for example, be 1-(2-iodoethoxy)-4-nitrobenzene, 1-(2-bromoethoxy)-4-nitrobenzene, 1-(2-chloroethoxy)-4-nitrobenzene or 1-chloromethoxy-4-nitrobenzene.

Further, in a case where $Y^1$ is —O—, $Y^2$ is a single bond and a is 0, as a method for preparing such a compound represented by the formula (3), a method of reacting a corresponding compound represented by the following formula (14) and a hydroxy group-substituted 4-nitrobenzene derivative in the presence of an alkali may, for example, be mentioned. The reaction solvent and the reaction temperature are in accordance with the above. However, a protic solvent such as an alcohol solvent or water may be used so long as it does not react with the raw material.

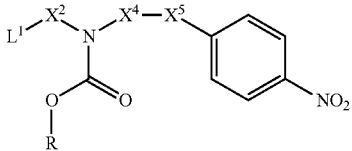

(14)

In the formula (14), $X^2$, $X^4$ and $X^5$ are as defined for the above formula (1), and $L^1$ is as defined for the above formula (9).

The hydroxy group-substituted 4-nitrobenzene derivative is in accordance with the above.

The method for preparing the compound represented by the formula (14) is not particularly limited. For example, the compound represented by the formula (14) may be prepared in the same manner as the method for preparing the compound represented by the formula (9) from the compound represented by the formula (8), using a corresponding compound represented by the following formula (15).

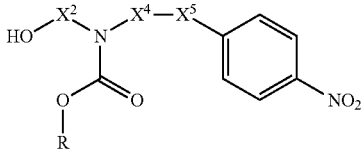

(15)

In the formula (15), $X^2$, $X^4$ and $X^5$ are as defined for the above formula (1).

In a case where $X^2$ in the compound represented by the formula (14) is $CH_2$ and $L^1$ is a chlorine atom, as another method for preparing such a compound represented by the formula (14), a method of reacting a corresponding N-alkoxycarbonyl-4-nitrophenylalkylamine and chlorotrimethylsilane and paraformaldehyde may be mentioned.

The method for preparing the N-alkoxycarbonyl-4-nitrophenylalkylamine is not particularly limited. For example, the same method as the method for preparing the compound represented by the formula (3) from the compound represented by the formula (4), using a corresponding 4-nitrophenylalkylamine, may be employed.

The method for preparing the compound represented by the formula (15) is not particularly limited. For example, the same method as the method of hydroxyalkylating the amine or the monohydroxyalkylamine, using a corresponding N-alkoxycarbonyl-4-nitrophenylalkylamine, may be employed.

<Polyimide Precursor>

The polyimide precursor of the present invention such as a polyamic acid or a polyamic acid ester may be obtained by reacting the specific diamine of the present invention and at least one member selected from the group consisting of tetracarboxylic acid and a tetracarboxylic acid derivative.

In a case where the polyimide precursor of the present invention is to be obtained, another diamine may be used in combination with the specific diamine of the present invention.

Specific examples of such another diamine include an aromatic diamine such as p-phenylenediamine, 2,3,5,6-tetramethyl-p-phenylenediamine, 2,5-dimethyl-p-phenylenediamine, m-phenylenediamine, 2,4-dimethyl-m-phenylenediamine, 2,5-diaminotoluene, 2,6-diaminotoluene, 2,5-diaminophenol, 2,4-diaminophenol, 3,5-diaminophenol, 3,5-diaminobenzyl alcohol, 2,4-diaminobenzyl alcohol, 4,6-diaminoresorcinol, 4,4'-diaminobiphenyl, 3,3'-dimethyl-4,4'-diaminobiphenyl, 3,3'-dimethoxy-4,4'-diaminobiphenyl, 3,3'-dihydroxy-4,4'-diaminobiphenyl, 3,3'-dicarboxy-4,4'-diaminobiphenyl, 3,3'-difluoro-4,4'-biphenyl, 3,3'-trifluoromethyl-4,4'-diaminobiphenyl, 3,4'-diaminobiphenyl, 3,3'-diaminobiphenyl, 2,2'-diaminobiphenyl, 2,3'-diaminobiphenyl, 4,4'-diaminodiphenylmethane, 3,3'-diaminodiphenylmethane, 3,4'-diaminodiphenylmethane, 2,2'-diaminodiphenylmethane, 2,3'-diaminodiphenylmethane, 4,4'-diaminodiphenyl ether, 3,3'-diaminodiphenyl ether, 3,4'-diaminodiphenyl ether, 2,2'-diaminodiphenyl ether, 2,3'-diaminodiphenyl ether, 4,4'-sulfonyldianiline, 3,3'-sulfonyldianiline, bis(4-aminophenyl)silane, bis(3-aminophenyl)silane, dimethyl-bis(4-aminophenyl)silane, dimethyl-bis(3-aminophenyl)silane, 4,4'-thiodianiline, 3,3'-thiodianiline, 4,4'-diaminodiphenylamine, 3,3'-diaminodiphenylamine, 3,4'-diaminodipheylamine, 2,2'-diaminodiphenylamine, 2,3'-diaminodiphenylamine, N-methyl(4,4'-diaminodiphenyl)amine, N-methyl(3,3'-diaminodiphenyl)amine, N-methyl(3,4'-diaminodiphenyl)amine, N-methyl(2,2'-diaminodiphenyl)amine, N-methyl(2,3'-diaminodiphenyl)amine, 4,4'-diaminobenzophenone, 3,3'-diaminobenzophenone, 3,4'-diaminobenzophenone, 1,4-diaminonaphthalene, 2,2'-diaminobenzophenone, 2,3'-diaminobenzophenone, 1,5-diaminonaphthalene, 1,6-diaminonaphthalene, 1,7-diaminonaphthalene, 1,8-diaminonaphthalene, 2,5-diaminonaphthalene, 2,6-diaminonaphthalene, 2,7-diaminonaphthalene, 2,8-diaminonaphthalene, 1,2-bis(4-aminophenyl)ethane, 1,2-bis(3-aminophenyl)ethane, 1,3-bis(4-aminophenyl)propane, 1,3-bis(3-aminophenyl)propane, 1,4-bis(4-aminophenyl)butane, 1,4-bis(3-aminophenyl)butane, bis(3,5-diethyl-4-aminophenyl)methane, 1,4-bis(4-aminophenoxy)benzene, 1,3-bis(4-aminophenoxy)benzene, 1,4-bis(4-aminophenyl)benzene, 1,3-bis(4-aminophenyl)benzene, 1,4-bis(4-aminobenzyl)benzene, 1,3-bis(4-aminophenoxy)benzene, 4,4'-[1,4-phenylenebis(methylene)]dianiline, 4,4-[1,3-phenylenebis(methylene)]dianiline, 3,4'-[1,4-phenylenebis(methylene)]dianiline, 3,4'-[1,3-phenylenebis(methylene)]dianiline, 3,3'-[1,4-phenylenebis(methylene)]dianiline, 3,3'-[1,3-phenylenebis(methylene)]dianiline, 1,4-phenylenebis[(4-aminophenyl)methanone], 1,4-phenylenebis[(3-aminophenyl)methanone], 1,3-phenylenebis[(4-aminophenyl)methanone], 1,3-phenylenebis[(3-aminophenyl)methanone], 1,4-phenylenebis(4-aminobenzoate), 1,4-phenylenebis(3-aminobenzoate), 1,3-phenylenebis(4-aminobenzoate), 1,3-phenylenebis(3-aminobenzoate), bis(4-aminophenyl)terephthalate, bis(3-aminophenyl)terephthalate, bis(4-aminophenyl)isophthalate, bis(3-aminophenyl)isophthalate, N,N'-(1,4-phenylene)bis(4-aminobenzamide), N,N'-(1,3-phenylene)bis(4-aminobenzamide), N,N'-(1,4-phenylene)bis(3-aminobenzamide), N,N'-(11,3-phenylene)bis(3-aminobenzamide), N,N'-bis(4-aminophenyl)terephthalamide, N,N'-bis(3-aminophenyl)terephthalamide, N,N'-bis(4-aminophenyl)isophthalamide, N,N'-bis(3-aminophenyl)isophthalamide, 9,10-bis(4-aminophenyl)anthracene, 4,4'-bis(4-aminophenoxy)diphenylsulfone, 2,2'-bis[4-(4-aminophenoxy)phenyl]propane, 2,2'-bis[4-(4-aminophenoxy)phenyl]hexafluoropropane, 2,2'-bis(4-aminophenyl)hexafluoropropane, 2,2'-bis(3-aminophenyl)hexafluoropropane, 2,2'-bis(3-amino-4-methylphenyl)hexafluoropropane, 2,2'-bis(4-aminophenyl)propane, 2,2'-bis(3-aminophenyl)propane, 2,2'-bis(3-amino-4-methylphenyl)propane, 3,5-diaminobenzoic acid, 2,5-diaminobenzoic acid, 1,3-bis(4-aminophenoxy)propane, 1,3-bis(3-aminophenoxy)propane, 1,4-bis(4-aminophenoxy)butane, 1,4-bis(3-aminophenoxy)butane, 1,5-bis(4-aminophenoxy)pentane, 1,5-bis(3-aminophenoxy)pentane, 1,6-bis(4-aminophenoxy)hexane, 1,6-bis(3-aminophenoxy)hexane, 1,7-bis(4-aminophenoxy)heptane, 1,7-bis(3-aminophenoxy)heptane, 1,8-bis(4-aminophenoxy)octane, 1,8-bis(3-aminophenoxy)octane, 1,9-bis(4-aminophenoxy)nonane, 1,9-bis(3-aminophenoxy)nonane, 1,10-bis(4-aminophenoxy)decane, 1,10-bis(3-aminophenoxy)decane, 1,11-bis(4-aminophenoxy)undecane, 1,11-bis(3-aminophenoxy)undecane, 1,12-bis(4-aminophenoxy)dodecane and 1,12-bis(3-aminophenoxy)dodecane; an alicyclic diamine such as bis(4-aminocyclohexyl)methane and bis(4-amino-3-methylcyclohexyl)methane; and an aliphatic diamine such as 1,3-diaminopropane, 1,4-diaminobutane, 1,5-diaminopentane, 1,6-diaminohexane, 1,7-diaminoheptane, 1,8-diaminooctane, 1,9-diaminononane, 1,10-diaminodecane, 1,11

<Production of Polyimide Precursor (Polyamic Acid)>

The polyamic acid as the polyimide precursor in the present invention is obtained by reaction of a diamine component containing the specific diamine and a tetracarboxylic acid dianhydride. The tetracarboxylic acid dianhydride is represented by the following formula (311):

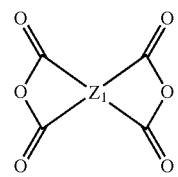

[311]

wherein $Z_1$ is a $C_{4-13}$ tetravalent organic group and includes a $C_{4-6}$ non-aromatic cyclic hydrocarbon group.

Preferred specific examples of $Z_1$ are represented by the following formulae [311a] to [311j]:

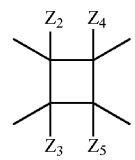

[311a]

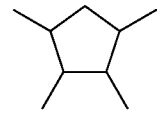

[311b]

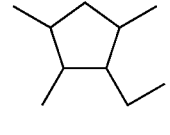

[311c]

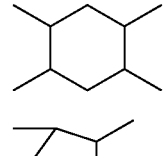

[311d]

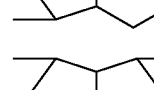

[311e]

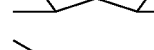

[311f]

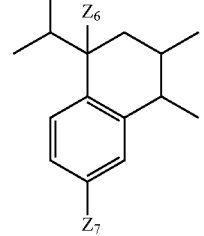

[311g]

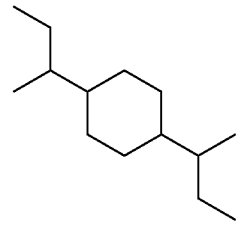

[311h]

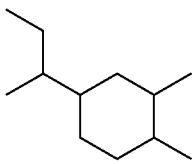
[311i]

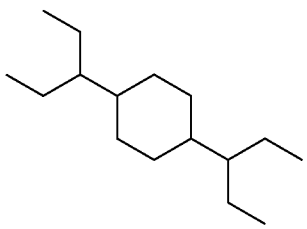
[311j]

In the formula [311a], each of $Z_2$ to $Z_5$ which may be the same or different from one another, is a group selected from the group consisting of a hydrogen atom, a methyl group, a chlorine atom and a benzene ring.

Each of $Z_6$ and $Z_7$ which may be the same or different from each other, is a hydrogen atom or a methyl group.

$Z_1$ is particularly preferably the formula [311a], [311c], [311d], [311e], [311f] or [311g] in view of polymerizability and easiness of preparation.

In the present invention, one or more may be selected from the above tetracarboxylic acid dianhydrides considering the properties such as the liquid crystal alignment property, the voltage retention property and the accumulated charge.

The polyamic acid of the present invention is a polyimide precursor obtained by polycondensation of the diamine component containing the above specific diamine and the tetracarboxylic acid dianhydride.

To obtain the polyimide precursor of the present invention by polycondensation of the diamine component and the tetracarboxylic acid dianhydride, a known preparation means may be employed. For example, a method of reacting the diamine component and the tetracarboxylic acid dianhydride in an organic solvent may be employed. This method is preferred in that the reaction will proceed relatively efficiently in the organic solvent and little by-product will form.

The organic solvent used for the reaction of the diamine component and the tetracarboxylic acid dianhydride is not particularly limited so long as the formed polyamide acid is soluble in it.

For reaction of the diamine component and the tetracarboxylic acid dianhydride in an organic solvent, a method of adding the tetracarboxylic acid dianhydride as it is or as dispersed or dissolved in an organic solvent to a dispersion or solution having the diamine component dispersed or dissolved in an organic solvent with stirring may be employed. On the contrary, a method of adding the diamine component to a dispersion or solution having the tetracarboxylic acid dianhydride dispersed or dissolved in an organic solvent, a method of alternately adding the tetracarboxylic acid dianhydride and the diamine component, etc. may also be mentioned. In the present invention, any of such methods may be employed. Further, in a case where each of the diamine component and the tetracarboxylic acid dianhydride comprises a plurality of compounds, the respective compounds may be reacted as mixed, they may be separately reacted sequentially, or they may be separately reacted to form low molecular weight products, which are mixed and reacted to form a high molecular weight product.

The temperature at which the diamine component and the tetracarboxylic acid dianhydride are reacted is properly selected within a range of from −20 to 150° C., and is preferably within a range from −5 to 100° C. considering the reaction efficiency. Further, the reaction may be carried out at an optional concentration. However, if the concentration is too low, a high molecular weight polyimide precursor will hardly be obtained. On the other hand, if the concentration is too high, the viscosity of the reaction liquid tends to be too high, and uniform stirring tends to be difficult. Accordingly, the concentration is preferably from 1 to 50 mass %, more preferably from 5 to 30 mass %. Further, the reaction may be carried out at high concentration at the initial stage and then an organic solvent may be added.

In the polymerization reaction to obtain the polyamic acid, the total number of moles of the diamine component is preferably from 0.8 to 1.2 by the ratio to the total number of moles of the tetracarboxylic acid dianhydride. Like usual polycondensation, the closer to 1.0 the molar ratio is, the higher the molecular weight of the polymer to be formed will be. Accordingly, the total molar ratio can be properly determined depending upon the situation.

<Production of Polyimide Precursor (Polyamic Acid Ester)>

In a case where the polyimide precursor of the present invention is a polyamic acid ester, it may be produced by the following process (A), (B) or (C).

(A) Production from Polyamic Acid

The polyamic acid ester may be produced by esterifying the above-produced polyamic acid. Specifically, it may be produced by reacting the polyamic acid and an esterifying agent in the presence of a solvent at from −20 to 150° C., preferably from 0 to 50° C. for from 30 minutes to 24 hours, preferably from 1 to 4 hours.

The esterifying agent is preferably one which can readily be removed by purification, and may, for example, be N,N-dimethylformamide dimethyl acetal, N,N-dimethylformamide diethyl acetal, N,N-dimethylformamide dipropyl acetal, N,N-dimethylformamide dineopentylbutyl acetal, N,N-dimethylformamide di-t-butyl acetal, 1-methyl-3-p-tolyltriazene, 1-ethyl-3-p-tolyltriazene, 1-propyl-3-p-tolyltriazene or 4-(4,6-dimethoxy-1,3,5-triazin-2-yl)-4-methylmorpholinium chloride. The amount of the esterifying agent is preferably from 2 to 6 moles per 1 mole of the repeating units of the polyamic acid.

The solvent to be used for the above reaction is preferably N,N-dimethylformamide, N-methyl-2-pyrrolidone or γ-butyrolactone in view of the solubility of the polymer, and they may be used alone or as a mixture of two or more. The polymer concentration at the time of production is preferably from 1 to 30 mass %, more preferably from 5 to 20 mass %, whereby precipitation of the polymer is less likely to occur, and a high molecular weight product tends to be obtained.

(B) Production by Reaction of Tetracarboxylic Acid Diester Dichloride and Diamine The polyamic acid ester may be produced from tetracarboxylic acid diester dichloride and a diamine containing the specific diamine.

Specifically, the polyamic acid ester can be produced by reacting tetracarboxylic acid diester dichloride and a diamine in the presence of a base and a solvent at from −20 to 150° C., preferably from 0 to 50° C. for from 30 minutes to 24 hours, preferably from 1 to 4 hours.

As the base, pyridine, triethylamine, 4-dimethylaminopyridine or the like may be used, and pyridine is preferred, whereby the reaction will moderately proceed. The amount of the base is preferably from 2 to 4 molar times based on tetracarboxylic acid diester dichloride, whereby the base will easily be removed, and a high molecular weight product tends to be obtained.

The solvent to be used for the above reaction is preferably N-methyl-2-pyrrolidone or γ-butyrolactone in view of the solubility of the monomer and the polymer, and they may be used alone or as a mixture of two or more. The polymer concentration at the time of production is preferably from 1 to 30 mass %, more preferably from 5 to 20 mass %, whereby precipitation of the polymer is less likely to occur, and a high molecular weight product tends to be obtained. Further, in order to prevent hydrolysis of tetracarboxylic acid diester dichloride, the solvent to be used for production of the polyamic acid ester is preferably dehydrated as far as possible, and it is preferred to carry out the reaction in a nitrogen atmosphere while inclusion of outdoor air is prevented.

(C) Production from Tetracarboxylic Acid Diester and Diamine

The polyamic acid ester may be produced by subjecting tetracarboxylic acid diester and a diamine containing the specific diamine to polycondensation.

Specifically, the polyamic acid ester may be produced by reacting tetracarboxylic acid diester and a diamine in the presence of a condensation agent, a base and a solvent at from 0 to 150° C., preferably from 0 to 100° C. for from 30 minutes to 24 hours, preferably from 3 to 15 hours.

The condensation agent may, for example, be triphenyl phosphite, dicyclohexylcarbodiimide, 1-ethyl-3-(3-dimethylaminopropyl)carbodiimide hydrochloride, N,N'-carbonyldiimidazole, dimethoxy-1,3,5-triazinylmethyl morpholinium, O-(benzotriazol-1-yl)-N,N,N',N'-tetramethyluronium tetrafluoroborate, O-(benzotriazol-1-yl)-N,N,N',N'-tetramethyluronium hexafluorophosphate or diphenyl(2,3-dihydro-2-thioxo-3-benzoxazolyl)phosphonate. The amount of the condensation agent is preferably from 2 to 3 molar times based on tetracarboxylic acid diester.

As the base, a tertiary amine such as pyridine or triethylamine may be used. The amount of the base is preferably from 2 to 4 molar times based on the diamine component, whereby the base will easily be removed, and a high molecular weight product tends to be obtained.

Further, in the above reaction, the reaction will efficiently proceed by adding a Lewis acid as an additive. The Lewis acid is preferably a lithium halide such as lithium chloride or lithium bromide. The amount of the Lewis acid is preferably from 0 to 1.0 molar time based on the diamine component.

Among the above three processes for producing the polyamic acid ester, particularly preferred is the process (A) or (B), whereby a high molecular weight polyamic acid ester will be obtained.

By pouring the solution of the polyamic acid ester obtained as mentioned above into a poor solvent with well stirring, the polymer can be precipitated. Precipitation is carried out several times, and the precipitates are washed with a poor solvent and dried at room temperature or by heating, whereby a powder of a purified polyamic acid ester can be obtained. The poor solvent is not particularly limited and may, for example, be water, methanol, ethanol, hexane, butyl cellosolve, acetone or toluene.

<Polyimide>

The polyimide can be obtained by subjecting the above polyimide precursor to dehydration ring closure. In the polyimide, the dehydration ring closure degree (imidization degree) of the polyimide precursor is not necessarily 100%, and it may be adjusted, for example, to be within a range of from 45 to 85% depending upon the purpose of use and the application.

As a method for imidizing the polyimide precursor, thermal imidization of heating a solution of the polyimide precursor as it is, or catalytic imidization of adding a catalyst to a solution of the polyimide precursor, may, for example, be mentioned.

In a case where the polyimide precursor is subjected to thermal imidization in a solution, the thermal imidization is carried out at a temperature of from 100 to 400° C., preferably from 120 to 250° C., and it is carried out preferably while water formed by the imidization reaction is discharged to the outside of the system.

The catalytic imidization of the polyimide precursor is carried out by adding a basic catalyst and an acid anhydride to a solution of the polyimide precursor, followed by stirring at from −20 to 250° C., preferably from 0 to 180° C. The amount of the basic catalyst is from 0.5 to 30 molar times, preferably from 2 to 20 molar times the amount of the amide acid groups, and the amount of the acid anhydride is from 1 to 50 molar times, preferably from 3 to 30 molar times the amount of the amide acid groups.

The basic catalyst may be pyridine, triethylamine, trimethylamine, tributylamine or trioctylamine, and among them, pyridine is preferred in that it has appropriate basicity to make the reaction proceed. The acid anhydride may be acetic anhydride, trimellitic anhydride or pyromellitic anhydride, and among them, acetic anhydride is preferred in that purification after completion of the reaction will easily be carried out. The imidization degree by catalytic imidization may be controlled by adjusting the amount of the catalyst, the reaction temperature and the reaction time.

To recover the formed polyimide precursor or polyimide from the reaction solution of the polyimide precursor or polyimide, the reaction solution is poured into a poor solvent to precipitate the polyimide precursor or polyimide. The poor solvent to be used for precipitation may be methanol, acetone, hexane, butyl cellosolve, heptane, methyl ethyl ketone, methyl isobutyl ketone, ethanol, toluene, benzene or water. The reaction solution is poured into the poor solvent, and the precipitated polymer is recovered by filtration, and dried under normal pressure or under reduced pressure at room temperature or by heating. Further, by repeating an operation of dissolving the precipitated and recovered polymer again in an organic solvent and precipitating and recovering it again, from 2 to 10 times, impurities in the polymer can be reduced. The poor solvent on that occasion may, for example, be an alcohol, a ketone or a hydrocarbon, and it is preferred to use at least three types of poor solvent selected from them, whereby purification efficiency will further improve.

The molecular weight of at least one polymer selected from the group consisting of the polyimide precursor and imidized polymer of the polyimide precursor thus obtained is, when the polymer is used as a component of a liquid crystal aligning agent, preferably from 2,000 to 500,000, more preferably from 5,000 to 300,000, further preferably from 10,000 to 100,000 by the weight average molecular weight. Further, the number average molecular weight is preferably from 1,000 to 250,000, more preferably from 2,500 to 150,000, further preferably from 5,000 to 50,000.

In the polyimide precursor and polyimide obtained by using the diamine of the present invention, the —C(=O)OR group on the N atom leaves by heating to form a NH group.

The heating temperature is at least a temperature at which the —C(C=O)OR group leaves and at most a temperature at which the application of the polyimide or the polyimide precursor is not influenced, and is preferably from 100 to 400° C., more preferably from 200 to 250° C.

EXAMPLES

Now, the present invention will be described in further detail with reference to Examples. However, it should be understood that the present invention is by no means restricted thereto.

Abbreviations and structures of compounds and methods for measuring the respective properties are shown below.

Boc: t-Butoxycarbonyl group
DMF: N,N-Dimethylformamide
THF: Tetrahydrofuran
NMP: N-Methyl-2-pyrrolidone
BCS: Butyl cellosolve
DA-A: N-tert-Butoxycarbonyl-N-(2-(4-aminophenyl)ethyl)-N-(4-aminobenzyl)amine
DA-B: N-(2-(4-aminophenyl)ethyl)-N-(4-aminobenzyl)amine
DA-C: N-tert-Butoxycarbonyl-N,N-bis(4-aminobenzyl)amine
DA-D: N-tert-Butoxycarbonyl-N-(2-(4-aminophenyl)ethyl)-N-(2-(4-aminophenoxy)ethyl)amine
DA-E: N-Methoxycarbonyl-N-(2-(4-aminophenyl)ethyl)-N-(4-aminobenzyl)amine
DA-F: N-Ethoxycarbonyl-N-(2-(4-aminophenyl)ethyl)-N-(4-aminobenzyl)amine
DA-G: N-Isopropyloxycarbonyl-N-(2-(4-aminophenyl)ethyl)-N-(4-aminobenzyl)amine
DA-H: N-Benzyloxycarbonyl-N-(2-(4-aminophenyl)ethyl)-N-(4-aminobenzyl)amine
DA-I: N-(9-Fluorenyl)methyloxycarbonyl-N-(2-(4-aminophenyl)ethyl)-N-(4-aminobenzyl)amine
DA-J: N-tert-Butoxycarbonyl-N,N-bis(2-(4-aminophenyloxy)ethyl)amine
DA-K: N-tert-Butoxycarbonyl-N-(4-aminophenyloxymethyl)-4-aminobenzylamine
DA-1: 1,2-Bis(4-aminophenoxy)ethane
DA-2: N-2-(4-Aminophenylethyl)-methylamine

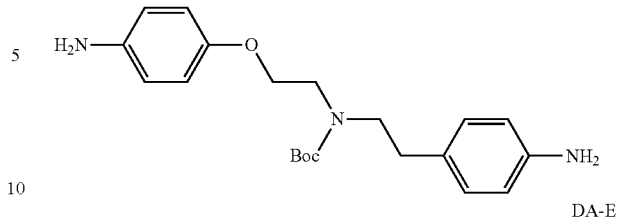

DA-A

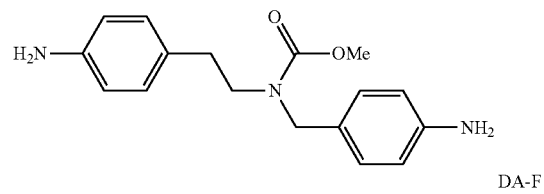

DA-B

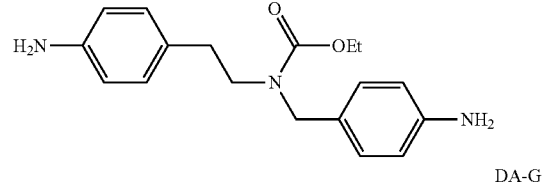

DA-C

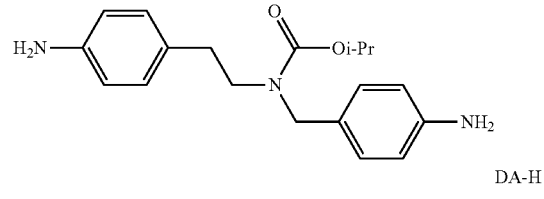

DA-D

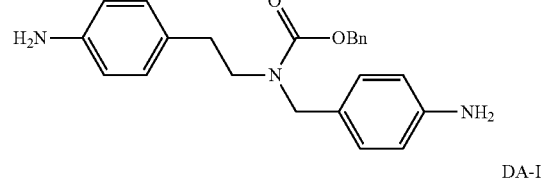

DA-E

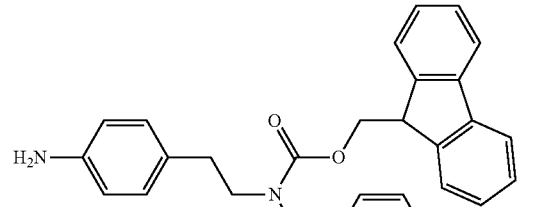

DA-F

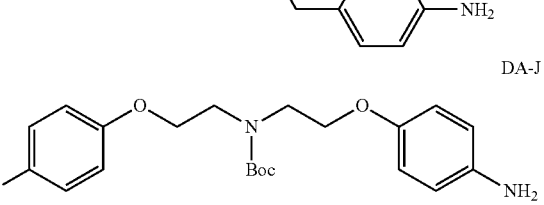

DA-G

DA-H

DA-I

DA-J

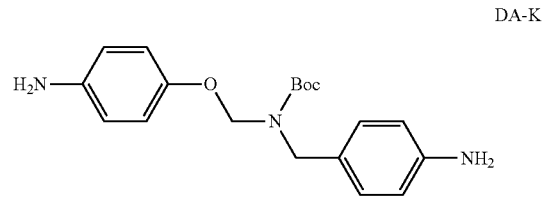

DA-K

-continued

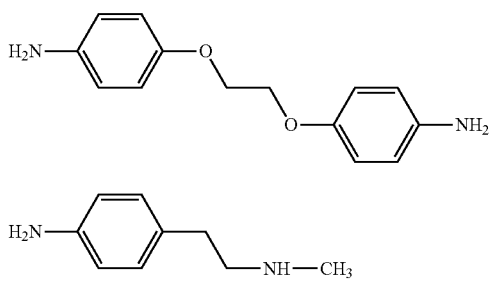

DA-1

DA-2

[¹H NMR]

Apparatus: Fourier transform superconducting nuclear magnetic resonance apparatus (FT-NMR) INOVA-400 (manufactured by Varian) 400 MHz Solvent: Deuterated chloroform ($CDCl_3$) or deuterated dimethyl sulfoxide (DMSO-$d_6$)

Standard substance: Tetramethylsilane (TMS)

Number of scans: 8 or 32

[¹³C{¹H}NMR]

Apparatus: Fourier transform superconducting nuclear magnetic resonance apparatus (FT-NMR) INOVA-400 (manufactured by Varian) 100 MHz Solvent: Deuterated chloroform ($CDCl_3$) or deuterated dimethyl sulfoxide (DMSO-$d_6$)

Standard substance: Tetramethylsilane (TMS)

Number of scans: 256

[DSC]

Apparatus: Differential scanning calorimetry measuring apparatus DSCISTARe system (manufactured by Mettler-Toredo International Inc.)

Pan: sealed Au pan

Temperature-increasing rate: 10° C./min

Melting point: The lowest endothermic peak temperature was analyzed.

[Viscosity]

The viscosity of each of the polyamic acid ester and polyamic acid solutions was measured using an E type viscometer TVE-22H (manufactured by Toki Sangyo Co., Ltd.) with a sample amount of 1.1 mL (milliliter) with cone roter TE-1 (1°34', R24) at a temperature of 25° C.

[Molecular Weight]

With respect to the molecular weight of each of the polyimide precursor and its imidized polymer, the number average molecular weight (hereinafter sometimes referred to as Mn) and the weight average molecular weight (hereinafter sometimes referred to as Mw) as values as calculated as polyethylene glycol and polyethylene oxide, were calculated by measurement by a GPC (room temperature gel permeation chromatography) apparatus.

GPC apparatus: Shodex (GPC-101)

Column: Shodex (KD803 and KD805 in series)

Column temperature: 50° C.

Eluent: N,N-Dimethylformamide (as additives, 30 mmol/L of lithium bromide monohydrate (LiBr.$H_2O$), 30 mmol/L of phosphoric acid anhydrous crystals (o-phosphoric acid) and 10 ml/L of tetrahydrofuran (THF))

Flow rate: 1.0 ml/min

Standard sample for preparation of calibration curve: TSK standard polyethylene oxide (weight average molecular weight (Mw): about 900,000, 150,000, 100,000 and 30,000) manufactured by TOSOH CORPORATION, and polyethylene glycol (peak top molecular weight (Mp): about 12,000, 4,000 and 1,000) manufactured by Polymer Laboratories Ltd.

In order to prevent peaks from overlapping with one another, two kinds of samples i.e. a sample having four types of polymers with molecular weights of 900,000, 100,000, 12,000 and 1,000 mixed and a sample having three types of polymers with molecular weights of 150,000, 30,000 and 4,000 mixed, were separately subjected to measurement.

[Measurement of Imidization Degree]

20 mg of a polyimide powder was put in a NMR sample tube (NMR sampling tube standard, diameter: 5 (manufactured by KUSANO SCIENCE CORPORATION), deuterated dimethyl sulfoxide (DMSO-d6, 0.05 mass % TMS (tetramethylsilane) mixed) (0.53 ml) was added, and ultrasonic waves were applied to completely dissolve the polyimide powder. The solution was subjected to 500 MHz proton NMR measurement by a NMR measuring apparatus (JNW-ECA500) (manufactured by JEOL Ltd. DATUM Solution Business Operations). The imidization degree was determined in accordance with the following formula from the peak integrated value of proton derived from a structure which did not change between before and after the imidization as standard proton, and the peak integrated value of proton derived from the NH group of the amide acid which appeared in the vicinity of from 9.5 to 10.0 ppm.

$$\text{Imidization degree (\%)} = (1 - \alpha \cdot x/y) \times 100$$

In the above formula, x is the peak integrated value of proton derived from the NH group of the amide acid, y is the peak integrated value of standard proton, and a is the proportion of the number of standard proton per one proton derived from the NH group of the amide acid in the case of a polyamide acid (imidization degree: 0%).

Preparation Example 1

Preparation of aromatic diamine (DA-A): N-tert-butoxycarbonyl-N-(2-(4-aminophenyl)ethyl)-N-(4-aminobenzyl)amine DA-A was prepared in the following three steps. DA-A corresponds to the specific diamine.

First Step: Preparation of N-(2-(4-nitrophenyl)ethyl)-N-(4-nitrobenzyl)amine (DA-A-1)

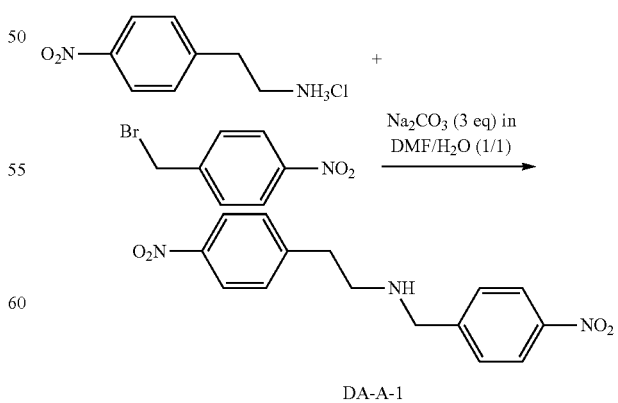

DA-A-1

2-(4-Nitrophenyl)ethylamine hydrochloride (50.0 g, 247 mmol) was dissolved in water (300 g) and DMF (50.0 g), sodium carbonate (78.4 g, 740 mmol) was added, and further, a DMF solution (200 g) of 4-nitrobenzyl bromide (53.3 g, 247 mmol) was dropwise added at 25° C. over a period of 1 hour. During dropwise addition, DMF/water=1/1 (w/w, 100 g) was further added to overcome stirring failure by precipitates.

Then, the mixture was stirred at room temperature for 20 hours and further stirred at 40° C. for 4 hours. Then, disappearance of the raw materials was confirmed by high performance liquid chromatography (hereinafter referred to simply as HPLC). Then, the reaction liquid was left to cool at room temperature, and the precipitates were collected by filtration, washed twice with water (150 g) and twice with 2-propanol (50.0 g) and vacuum dried at 50° C. to obtain N-2-(4-nitrophenyl)ethyl-N-(4-nitrobenzyl)amine (white solid, amount obtained: 73 g, yield: 99%).

$^1$H NMR (DMSO-d$_6$): δ 8.18 (d, J=8.8 Hz, 2H, C$_6$H$_4$), 8.15 (d, J=8.8 Hz, 2H, C$_6$H$_4$), 7.59, (d, J=8.8 Hz, 2H, C$_6$H$_4$), 7.52 (d, J=8.8 Hz, 2H, C$_6$H$_4$), 3.87 (s, 2H, CH$_2$), 2.91 (t, J=7.0 Hz, 2H, CH$_2$), 2.80 (t, J=7.0 Hz, 2H, CH$_2$), 2.46 (s, 1H, NH). $^{13}$C{$^1$H} NMR (DMSO-d$_6$): δ 149.8, 149.5, 146.6, 146.3, 130.3, 129.2, 123.7, 123.6, 52.4, 50.0, 36.0 (each s).

Melting point (DSC): 123° C.

Second Step: Preparation of N-tert-butoxycarbonyl-N-(2-(4-nitrophenyl)ethyl)-N-(4-nitrobenzyl)amine (DA-A-2)

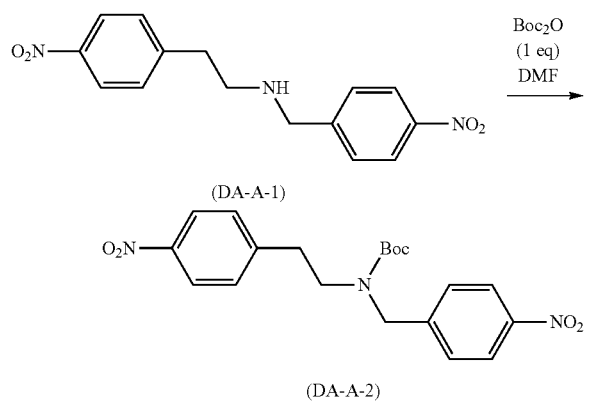

N-2-(4-Nitrophenyl)ethyl-N-4-nitrobenzylamine (73 g, 0.24 mol) was dissolved in DMF (371 g), and di-tert-butyl dicarbonate (54 g, 0.24 mol) was dropwise added at from 2 to 8° C. over a period of 10 minutes. Then, the mixture was stirred at 20° C. for 4 hours, and disappearance of the raw materials was confirmed by HPLC. Then, DMF was distilled off under reduced pressure, and the reaction liquid was mixed with ethyl acetate (371 g) and washed three times with water (371 g). Then, the organic layer was concentrated to obtain an orange oil (crude amount obtained: 96 g, crude yield: 97%). The crude product was purified by silica gel column chromatography (hexane/ethyl acetate=7/3 (v/v, Rf=0.3)) to obtain a yellow oil (crude amount obtained: 82.0 g, crude yield: 82.8% (two steps)).

The yellow oil was mixed with methanol (118 g) and dissolved at 50° C., and the solution was cooled with stirring, followed by stirring at from 0 to 5° C. for 30 minutes, and the solution was subjected to filtration, followed by drying to obtain N-tert-butoxycarbonyl-N-2-(4-nitrophenyl)ethyl-N-4-nitrobenzylamine (white powder, amount obtained: 74.5 g, yield: 78% (two steps)).

$^1$H NMR (DMSO-d$_6$): δ 8.22 (d, J=8.4 Hz, 2H, C$_6$H$_4$), 8.18-8.16 (br, 2H, C$_6$H$_4$), 7.51 (d, J=8.4 Hz, 2H, C$_6$H$_4$), 7.48 (br, 2H, C$_6$H$_4$), 4.57-4.54 (br, 2H, CH$_2$), 3.55-3.49 (br, 2H, CH$_2$), 2.97 (br, 2H, CH$_2$), 1.36-1.32 (br, 9H, tert-Bu). $^{13}$C{$^1$H} NMR (DMSO-d$_6$): δ 155.2, 154.8, 147.9, 147.5, 147.1, 147.0, 146.5, 130.6, 128.7, 128.4, 124.0, 123.8, 79.7, 50.3, 49.2, 48.4, 34.3, 34.0, 28.2 (each s).

Melting point (DSC): 77° C.

Third Step: Preparation of N-tert-butoxycarbonyl-N-(2-(4-aminophenyl)ethyl)-N-(4-aminobenzyl) amine (DA-A)

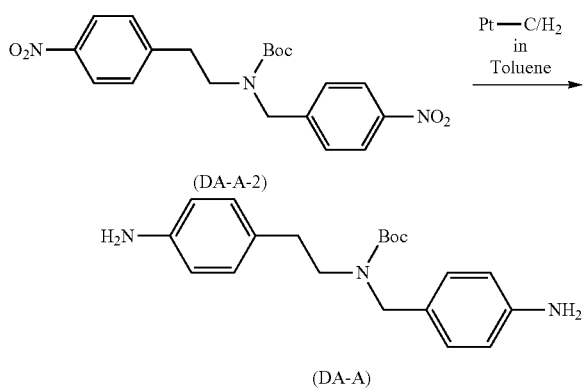

N-tert-Butoxycarbonyl-N-2-(4-nitrophenyl)ethyl-N-4-nitrobenzylamine (74 g, 0.18 mol) was dissolved in tetrahydrofuran (370 g), and 3 mass % platinum-carbon (7.4 g) was added, followed by stirring in a hydrogen atmosphere at room temperature for 72 hours. Disappearance of the raw material was confirmed by HPLC, the catalyst was removed by filtration, and the filtrate was concentrated and dried to obtain crude DA-A as a pale yellow oil (crude amount obtained: 66 g, crude yield: 105%). Then, the crude product was dissolved in toluene (198 g) at 80° C., followed by stirring at 2° C. for one hour to precipitate crystals. The precipitated crystals were collected by filtration and dried to obtain DA-A (white powder, amount obtained: 56 g, yield: 90%).

$^1$H NMR (DMSO-d$_6$): δ 6.92 (d, J=8.0 Hz, 2H, C$_6$H$_4$), 6.84-6.76 (br, 2H, C$_6$H$_4$), 6.54 (d, J=8.0 Hz, 2H, C$_6$H$_4$), 6.50 (d, J=8.0 Hz, 2H, C$_6$H$_4$), 4.98 (s, 2H, NH$_2$), 4.84 (s, 2H, NH$_2$), 4.16 (br, 2H, CH$_2$), 3.13 (br, 2H, CH$_2$), 2.51 (br, 2H, CH$_2$), 1.41 (s, 9H, tert-Bu). $^{13}$C{$^1$H} NMR (DMSO-d$_6$): δ 155.4, 154.9, 148.2, 147.2, 129.5, 129.3, 129.1, 128.9, 126.6, 125.7, 114.5, 114.3, 78.9, 78.8, 50.2, 49.2, 48.4, 33.9, 33.3, 28.5 (each s).

Melting point (DSC): 103° C.

Preparation Example 2

Into a 100 mL four-necked flask equipped with a stirring apparatus and a nitrogen introduction tube, 2.93 g (12.00 mmol) of DA-1 and 4.43 g (11.99 mmol) of DA-A were weighed, and 81.98 g of NMP was added, followed by stirring while nitrogen was supplied, to dissolve DA-1 and DA-A. 5.35 g (23.88 mmol) of 1,3-dimethyl-1,2,3,4-cyclobutanetetracarboxylic dianhydride was added to the resulting diamine solution with stirring, and 9.11 g of NMP was further added so that the solid content concentration would be 12 mass %, followed by stirring at room temperature for 24 hours to obtain a polyamic acid solution (PAA-1). The viscosity of the polyamic acid solution at a temperature of 25° C. was 205 mPa·s. Further, the molecular weight of the polyamic acid was Mn=10,530 and Mw=29,900.

Preparation Example 3

Into a 100 ml four-necked flask equipped with a stirring apparatus and a nitrogen introduction tube, 20 g of the polyamic acid solution (PAA-1) obtained in Preparation Example 2 was weighed, and 14.29 g of NMP was added, followed by stirring for 30 minutes. To the obtained polyamic acid solution, 1.48 g of acetic anhydride and 0.38 g of pyridine were added, followed by heating at 60° C. for 3 hours to conduct chemical imidization. The obtained reaction liquid was poured into 139 ml of methanol with stirring, and the obtained precipitate was collected by filtration and washed three times with 139 ml of methanol. The obtained resin powder was dried at 60° C. for 12 hours to obtain a polyimide resin powder.

Of the polyimide resin powder, the imidization degree was 75%, and the molecular weight was Mn=7,120 and Mw=12,485.

1.80 g of the obtained polyimide resin powder was put in a 200 ml Erlenmeyer flask in which a stirrer was put, and 13.20 g of NMP was added, followed by stirring at 40° C. for 24 hours to dissolve the polyimide resin powder to obtain a polyimide solution (PI-1).

Preparation Example 4

Into a 100 mL four-necked flask equipped with a stirring apparatus and a nitrogen introduction tube, 1.91 g (7.82 mmol) of DA-1, 1.56 g (10.40 mmol) of DA-2 and 2.67 g (7.81 mmol) of DA-A were weighed, and 55.18 g of NMP was added, followed by stirring while nitrogen was supplied to dissolve DA-1, DA-2 and DA-A. 5.22 g (23.92 mmol) of pyromellitic dianhydride was added to the resulting diamine solution with stirring, and 28.04 g of NMP was further added so that the solid content concentration would be 12 mass %, followed by stirring at room temperature for 24 hours to obtain a polyamic acid solution (PAA-2). The viscosity of the polyamic acid solution at a temperature of 25° C. was 600 mPa·s. Further, the molecular weight of the polyamic acid was Mn=17,370 and Mw=41,450.

Preparation Example 5

Into a 50 mL four-necked flask equipped with a stirring apparatus and a nitrogen introduction tube, 3.69 g (9.99 mmol) of DA-A was weighed, and 39.16 g of NMP was added, followed by stirring while nitrogen was supplied to dissolve DA-A. 2.24 g (9.98 mmol) of 1,3-dimethyl-1,2,3,4-cyclobutanetetracarboxylic dianhydride was added to the resulting diamine solution with stirring, and 4.35 g of NMP was further added so that the solid content concentration would be 12 mass %, followed by stirring at room temperature for 24 hours to obtain a polyamic acid solution (PAA-3). The viscosity of the polyamic acid solution at a temperature of 25° C. was 60 mPa·s. Further, the molecular weight of the polyamic acid was Mn=12,940 and Mw=28,468.

Preparation Example 6

Preparation of aromatic diamine (DA-A): N-tert-butoxycarbonyl-N-(2-(4-aminophenyl)ethyl)-N-(4-aminobenzyl)amine DA-A was prepared in the following three steps.

First Step: Preparation of N-(2-(4-nitrophenyl)ethyl)-N-(4-nitrobenzyl)amine (DA-A-1)

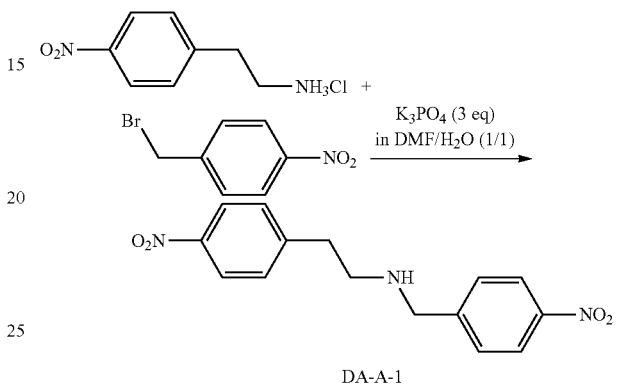

DA-A-1

2-(4-Nitrophenyl)ethylamine hydrochloride (150 g, 0.740 mol) was added to a mixture of water (300 g) and DMF (360 g), and a 33 mass % aqueous potassium phosphate solution (1,071 g, 2.22 mol) was dropwise added at 10° C. over a period of 10 minutes. The mixture was stirred for one hour, and a DMF solution (480 g) of 4-nitrobenzyl bromide (160 g, 0.740 mol) the temperature of which was adjusted to 10° C. was dropwise added at 10° C. over a period of 2 hours. Further, the container in which the DMF solution of 4-nitrobenzyl bromide was prepared was washed with DMF (54 g), and the washing liquid was added to the reaction mixture.

The reaction mixture was stirred at 10° C. for 16 hours, and disappearance of the raw materials was confirmed by HPLC. Then, the reaction mixture was stirred at 40° C. for one hour, and the precipitate was collected by filtration to obtain a recovered product.

Then, the recovered product was mixed with 2-methy-4-pentanone (1,115 g) and dissolved by heating at 65° C., followed by washing twice with water (446 g), and the organic layer was separated from water. The separated organic layer was cooled to 20° C., and the precipitated crystals were collected by filtration. The obtained crystals were vacuum dried at 50° C. to obtain N-2-(4-nitrophenyl)ethyl-N-(4-nitrobenzyl)amine (pale yellow solid, amount obtained: 166 g, yield: 74%).

Second Step: Preparation of N-tert-Butoxycarbonyl-N-(2-(4-nitrophenyl)ethyl)-N-(4-nitrobenzyl)amine (DA-A-2)

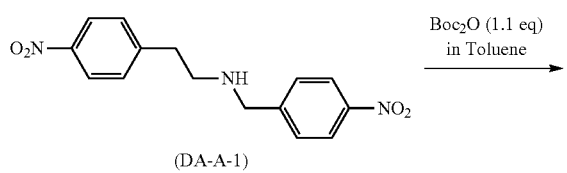

(DA-A-1)

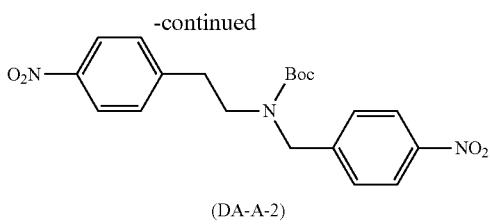

(DA-A-2)

N-2-(4-Nitrophenyl)ethyl-N-4-nitrobenzylamine (150 g, 0.498 mol) was added to toluene (150 g), and a toluene (30 g) solution of di-tert-butyl dicarbonate (120 g, 0.548 mol) was further dropwise added at 60° C. over a period of one hour. Further, the container in which the toluene solution of di-tert-butyl dicarbonate was prepared was washed with toluene (15 g), and the washing liquid was added to the reaction mixture.

Then, the reaction mixture was stirred at 60° C. for 30 minutes, and disappearance of the raw materials was confirmed by HPLC. Then, the reaction solution was cooled to 25° C., n-heptane (166 g) was dropwise added over a period of 20 minutes, followed by stirring for 30 minutes, and N-tert-butoxycarbonyl-N-2-(4-nitrophenyl)ethyl-N-4-nitrobenzylamine (0.15 g) as seed crystals was added, followed by stirring at 25° C. for 2 hours. Then, n-heptane (273 g) was dropwise added over a period of one and a half hours, followed by stirring for 15 hours, and the precipitated crystals were collected by filtration and vacuum dried at 50° C. to obtain N-tert-butoxycarbonyl-N-2-(4-nitrophenyl) ethyl-N-4-nitrobenzylamine (white powder, amount obtained: 191 g, yield: 96%).

Third Step: Preparation of N-tert-butoxycarbonyl-N-(2-(4-aminophenyl)ethyl)-N-(4-aminobenzyl)amine (DA-A)

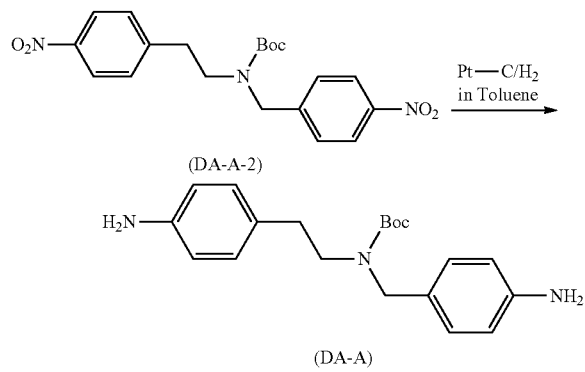

N-tert-Butoxycarbonyl-N-2-(4-nitrophenyl)ethyl-N-4-nitrobenzylamine (180 g, 0.448 mol) was dissolved in toluene (1,080 g), and 3 mass % platinum-carbon (9.0 g) was added, followed by stirring in a hydrogen atmosphere at room temperature for 48 hours. Disappearance of the raw material was confirmed by HPLC, and then the mixture was heated to 60° C. Further, the catalyst was removed by filtration, the reaction container was washed with 240 g of toluene, followed by filtration to obtain a filtrate. The filtrate was washed twice with water (72.0 g) at 60° C., and the organic layer was vacuum concentrated at 60° C. until 374 g of the residue was obtained. Then, the residue was cooled to 28° C., and DA-A (0.18 g) as seed crystals was added, followed by stirring for one hour, and the residue was cooled to 5° C. The residue was stirred further for 3 days, and the precipitated crystals were collected by filtration and vacuum dried at 50° C. to obtain DA-A (white powder, amount obtained: 137 g, yield: 89%).

Preparation Example 7

Preparation of aromatic diamine (DA-C):
N-tert-Butoxycarbonyl-N,N-bis(4-aminobenzyl)amine DA-C was prepared in the following three steps. DA-C corresponds to the specific diamine.

First Step: Preparation of bis(4-nitrobenzyl)amine (DA-C-1)

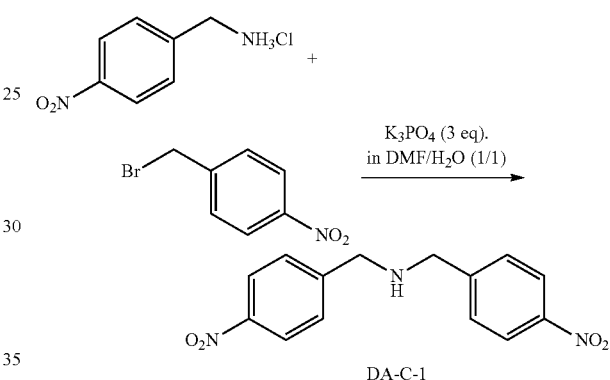

DA-C-1

4-Nitrobenzylamine hydrochloride (20.0 g, 106 mmol) was dissolved in water (40.0 g) and DMF (48.0 g), potassium phosphate (67.5 g, 318 mmol) dissolved in water (80.0 g) was added, and then a DMF solution (96.9 g) of 4-nitrobenzyl bromide (22.9 g, 106 mmol) was dropwise added at 10° C. Further, the container in which the DMF solution of 4-nitrobenzyl bromide was prepared was washed with DMF (8.0 g), and the washing liquid was added to the reaction mixture.

Then, the reaction mixture was stirred at 10° C. for 20 hours, and disappearance of the raw materials was confirmed by HPLC. Then, the reaction liquid was recovered to room temperature, and the precipitate was collected by filtration and washed once with DMF (20 g). The obtained product was dissolved in 2-methyl-4-pentanone (148.6 g) and washed twice with water (60.0 g). The organic layer was cooled to 10° C., and the resulting precipitate was collected by filtration and vacuum dried at 50° C. to obtain bis(4-nitrobenzyl)amine (white powder, amount obtained: 12.7 g, yield: 42%).

$^1$H NMR (CDCl$_3$): δ 8.19 (d, J=8.8 Hz, 4H, C$_6$H$_4$), 7.55 (d, J=8.8 Hz, 4H, C$_6$H$_4$), 3.95 (s, 4H, CH$_2$). $^{13}$C{$^1$H} NMR (CDCl$_3$): δ 147.6, 147.1, 128.6, 123.7, 52.4 (each s).

Melting point (DSC): 97° C.

Second Step: Preparation of N-tert-Butoxycarbonyl-N,N-bis(4-nitrobenzyl)amine (DA-C-2)

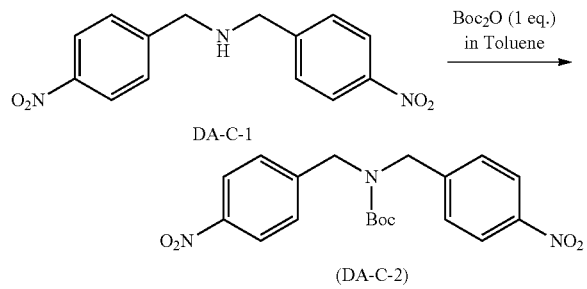

Bis(4-nitrobenzyl)amine (12.0 g, 41.8 mmol) was dissolved in a toluene solution (31.9 g) of di-tert-butyl dicarbonate (9.57 g, 43.9 mmol).

Then, the solution was stirred at 70° C. for one hour, and disappearance of the raw materials was confirmed by HPLC. Then, toluene was distilled off under reduced pressure, and to the obtained residue, toluene (15.6 g) and n-heptane (13.2 g) were added, followed by stirring at room temperature. Further, n-heptane (24.0 g) was slowly added, and after formation of a precipitate was confirmed, the mixture was cooled to 10° C. with stirring, and 12 hours later, the precipitate was collected by filtration and dried to obtain N-tert-butoxycarbonyl-N,N-bis(4-nitrobenzyl)amine (white powder, amount obtained: 15.3 g, yield: 95%).

$^1$H NMR (CDCl$_3$): δ 8.20 (d, J=8.4 Hz, 4H, C$_6$H$_4$), 7.39 (br, 4H, C$_6$H$_4$), 4.53 (br, 4H, CH$_2$), 1.48 (br, 9H, tert-Bu). $^{13}$C{$^1$H} NMR (CDCl$_3$): δ 155.5, 147.3, 145.1, 128.4, 127.7, 123.9, 81.4, 49.9, 49.6, 28.3 (each s).

Melting point (DSC): 81° C.

Third Step: Preparation of N-tert-Butoxycarbonyl-N,N-bis(4-aminobenzyl)amine (DA-C)

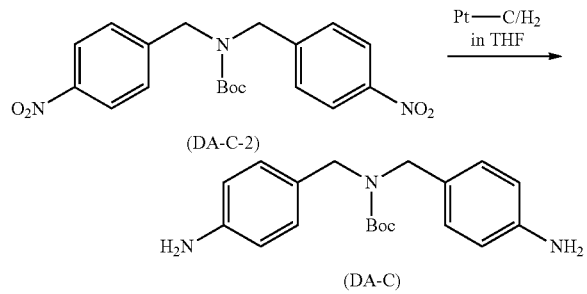

N-tert-Butoxycarbonyl-N,N-bis(4-nitrobenzyl)amine (14.0 g, 36.1 mmol) was dissolved in tetrahydrofuran (84 g), and 3 mass % platinum-carbon (0.4 g) was added, followed by stirring in a hydrogen atmosphere at room temperature for 4 hours. Disappearance of the raw material was confirmed by HPLC, the catalyst was removed by filtration, and the filtrate was concentrated. The concentrate was dissolved in toluene (84.0 g), followed by stirring at 5° C. for one hour to precipitate crystals. The precipitated crystals were collected by filtration and dried to obtain DA-C (white powder, amount obtained: 11 g, yield: 90%).

$^1$H NMR (CDCl$_3$): δ 7.03 (br, 2H, C$_6$H$_4$), 7.00 (br, 2H, C$_6$H$_4$), 6.65 (d, J=8.0 Hz, 4H, C$_6$H$_4$), 4.27 (br, 2H, CH$_2$), 4.19 (br, 2H, CH$_2$), 3.97 (s, 4H, NH$_2$), 1.50 (s, 9H, tert-Bu). $^{13}$C{$^1$H} NMR (CDCl$_3$): δ 156.0, 145.6, 129.4, 128.8, 127.9, 115.1, 79.7, 48.2, 47.9, 28.5 (each s).

Melting point (DSC): 131° C.

Preparation Example 8

Preparation of aromatic diamine (DA-D): N-tert-butoxycarbonyl-N-(2-(4-aminophenyl)ethyl)-N-(2-(4-aminophenoxy)ethyl)amine DA-D was prepared in the following three steps. DA-D corresponds to the specific diamine.

First Step: Preparation of N-(2-(4-nitrophenyl)ethyl)-N-(2-(4-nitrophenoxy)ethyl)amine (DA-D-1)

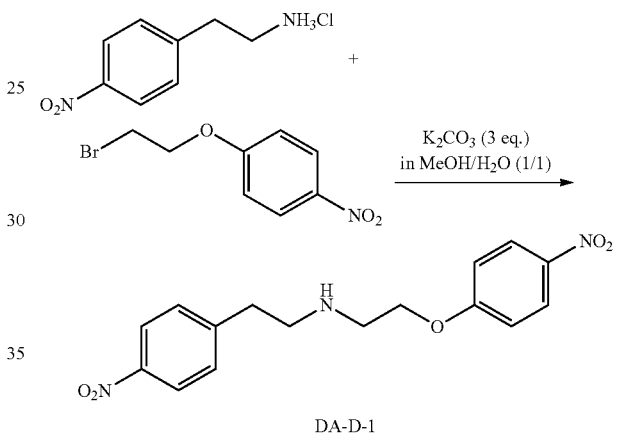

2-(4-Nitrophenyl)ethylamine hydrochloride (7.65 g, 37.8 mmol) was dissolved in water (15.3 g) and MeCN (acetonitrile) (15.3 g), and further, potassium carbonate (15.7 g, 114 mmol) dissolved in water (22.5 g) was added, and then a MeCN solution (30.4 g) of 4-nitrophenoxyethyl bromide (7.43 g, 30.2 mmol) was dropwise added at 20° C. Then, the reaction mixture was subjected to reflux for 7 hours, and disappearance of the raw materials was confirmed by HPLC. Then, the reaction liquid was left to cool at room temperature, and the aqueous layer was removed. Then, the organic layer was washed with water (31 g), followed by stirring at 5° C. for 30 minutes, and the precipitated solid was collected by filtration and washed twice with water (15 g). Toluene (80.0 g) and water (80 g) were added, followed by heating at 80° C. Then, a 3.2 mass % aqueous HCl solution (22 g) was added, and the organic layer was removed. The aqueous layer was washed twice with toluene (80 g), and a 1N aqueous NaOH solution (15.3 g) was added, and the mixture was cooled to 5° C., followed by stirring for 30 minutes. Then, the precipitated solid was collected by filtration, washed with water (60 g) and dried to obtain N-(2-(4-nitrophenyl)ethyl-N-(2-(4-nitrophenoxy)ethyl)amine (yellow powder, amount obtained: 2.7 g, yield: 27%).

$^1$H NMR (DMSO-d$_6$): δ 8.20 (d, J=9.2 Hz, 2H, C$_6$H$_4$), 8.14 (d, J=8.4 Hz, 2H, C$_6$H$_4$), 7.52 (d, J=8.4 Hz, 2H, C$_6$H$_4$), 7.13 (d, J=9.2 Hz, 2H, C$_6$H$_4$), 4.15 (t, J=5.6 Hz, 2H, OCH$_2$), 2.94 (t, J=5.6 Hz, 2H, CH$_2$Ar), 2.87 (br, 4H, CH$_2$NCH$_2$).

Second Step: Preparation of N-tert-butoxycarbonyl-N-(2-(4-nitrophenyl)ethyl-N-(2-(4-nitrophenoxy)ethyl)amine (DA-D-2)

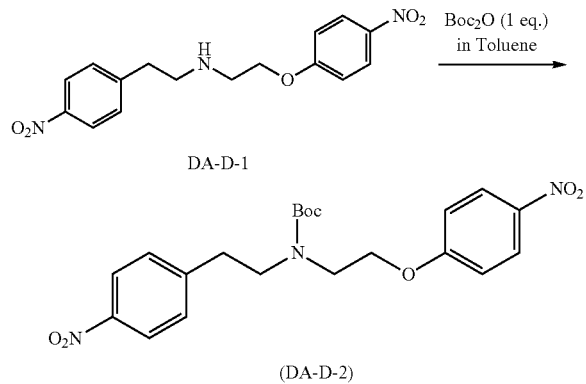

N-(2-(4-Nitrophenyl)ethyl-N-(2-(4-nitrophenoxy)ethyl)amine (5.55 g, 16.7 mmol) and triethylamine (1.86 g, 18.4 mmol) were dissolved in toluene (11.1 g), and a toluene solution (15.0 g) of di-tert-butyl dicarbonate (4.02 g, 18.4 mmol) was dropwise added. Then, the mixture was stirred at 70° C. for one hour, and disappearance of the raw materials was confirmed by HPLC. Then, water (55.0 g) was added, followed by washing twice. The mixture was left to cool at room temperature, n-heptane (22.1 g) was added, and after a solid was precipitated, the mixture was cooled to 5° C., followed by stirring for 30 minutes. Then, the precipitate was collected by filtration and dried to obtain N-tert-butoxycarbonyl-N-(2-(4-nitrophenyl)ethyl-N-(2-(4-nitrophenoxy)ethyl)amine (yellow powder, amount obtained: 6.6 g, yield: 93%).

$^1$H NMR (DMSO-$d_6$): δ 8.22-8.15 (br, 4H, $C_6H_4$), 7.50 (d, J=8.0 Hz, 2H, $C_6H_4$), 7.15 (d, J=9.2 Hz, 2H, $C_6H_4$), 4.21 (t, J=5.6 Hz, 2H, $OCH_2$), 3.57-3.49 (br, 4H, $CH_2NCH_2$), 2.96 (t, J=6.8 Hz, 2H, $CH_2Ar$), 1.30 (s, 9H, tert-Bu). $^{13}C\{^1H\}$ NMR (DMSO-$d_6$): δ 164.0, 154.8, 148.2, 146.5, 141.3, 130.7, 126.3, 123.9, 115.4, 79.4, 67.1, 49.2, 48.4, 46.0, 34.7, 34.0, 28.2 (each s).

Third Step: Preparation of N-tert-butoxycarbonyl-N-(2-(4-aminophenyl)ethyl)-N-(2-(4-aminophenoxy)ethyl)amine (DA-D)

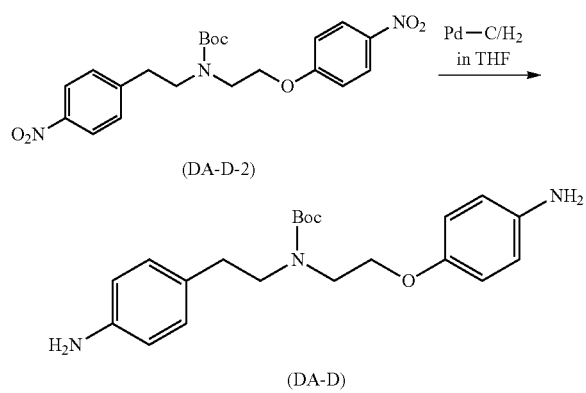

N-tert-Butoxycarbonyl-N-(2-(4-nitrophenyl)ethyl-N-(2-(4-nitrophenoxy)ethyl)amine (6.13 g, 14.2 mmol) was dissolved in tetrahydrofuran (36 g), and 5 mass % palladium-carbon (0.3 g) was added, followed by stirring in a hydrogen atmosphere at room temperature for 3 hours. Disappearance of the raw material was confirmed by HPLC, and then the catalyst was removed by filtration, and the filtrate was concentrated. The concentrate was mixed with toluene (36.0 g) and dissolved at 60° C., and washed twice with water (5.0 g). Then, the mixture was stirred at 0° C. for one hour to precipitate crystals. The precipitated crystals were collected by filtration and dried to obtain DA-D (pale purple powder, amount obtained: 4.5 g, yield: 85%).

$^1$H NMR (DMSO-$d_6$): δ 6.83 (d, J=7.6 Hz, 2H, $C_6H_4$), 6.64 (d, J=6.8 Hz, 2H, $C_6H_4$), 6.51 (d, J=6.8 Hz, 4H, $C_6H_4$), 4.86 (s, 2H, $NH_2$), 4.60 (s, 2H, $NH_2$), 3.85 (t, J=6.0 Hz, 2H, $OCH_2$), 3.39 (br, 2H, $CH_2N$), 3.32 (t, J=7.6 Hz, 2H, $NCH_2$), 2.61 (t, J=7.6 Hz, 2H, $CH_2Ar$), 1.39 (s, 9H, tert-Bu). $^{13}C\{^1H\}$ NMR (DMSO-$d_6$): δ 155.1, 150.1, 147.3, 142.9, 129.6, 126.5, 115.6, 115.4, 114.5, 79.0, 66.7, 50.8, 46.9, 34.3, 28.5 (each s).

Melting point (DSC): 100.1° C.

Preparation Example 9

Preparation of aromatic diamine (DA-E): N-methoxycarbonyl-N-(2-(4-aminophenyl)ethyl)-N-(4-aminobenzyl)amine DA-E was prepared in the following two steps. DA-E corresponds to the specific diamine.

First Step: Preparation of N-methoxycarbonyl-N-(2-(4-nitrophenyl)ethyl)-N-(4-nitrobenzyl)amine (DA-E-1)

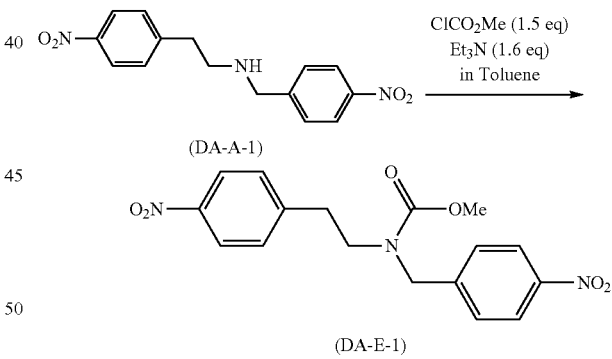

N-2-(4-Nitrophenyl)ethyl-N-4-nitrobenzylamine (35.0 g, 116 mmol) and triethylamine (15.3 g, 151 mmol) were added to toluene (350 g), the mixture was cooled to 4° C., and methyl chloroformate (13.2 g, 139 mmol) was dropwise added over a period of 30 minutes. Then, the mixture was stirred at 5° C. for one hour, and triethylamine (3.53 g, 34.9 mmol) and methyl chloroformate (3.29 g, 34.8 mmol) were further added, followed by stirring at from 10 to 30° C. for 30 minutes, and disappearance of the raw materials was confirmed by HPLC.

Then, the reaction mixture was heated to 60° C., and an operation of adding water (70 g) and disposing of the aqueous layer, was repeated three times. Then, the reaction mixture was cooled to 25° C., n-heptane (210 g) was added, the mixture was cooled to 5° C. and stirred for 17 hours, and then the precipitated solid was collected by filtration and dried to obtain N-methoxycarbonyl-N-(2-(4-nitrophenyl)ethyl)-N-(4-nitrobenzyl)amine (DA-E-1) (white powder, amount obtained: 38 g, yield: 93%).

$^1$H NMR (DMSO-d$_6$): δ 8.14 (d, J=8.8 Hz, 2H, C$_6$H$_4$), 8.10 (d, J=8.8 Hz, 2H, C$_6$H$_4$), 7.45-7.43 (br, 4H, C$_6$H$_4$), 4.42 (s, 2H, CH$_2$), 3.54-3.47 (m, 2H, CH$_2$), 3.51 (s, 3H, CH$_3$), 2.91 (t, J=7.0 Hz, 2H, CH$_2$). $^{13}$C{$^1$H} NMR (DMSO-d$_6$): δ 156.7, 147.7, 147.0, 146.7, 146.5, 130.5, 128.8, 128.4, 124.0, 123.8, 53.0, 50.3, 48.8, 48.2, 34.3, 33.8 (each s).

Second Step: Preparation of N-tert-methoxycarbonyl-N-(2-(4-aminophenyl)ethyl)-N-(4-aminobenzyl)amine (DA-E)

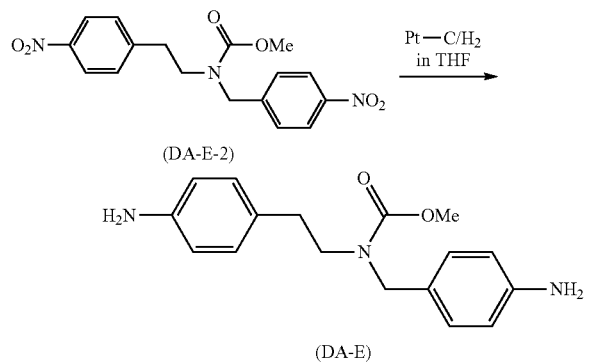

N-Methoxycarbonyl-N-2-(4-nitrophenyl)ethyl-N-4-nitrobenzylamine (30.0 g, 83.5 mmol) was dissolved in tetrahydrofuran (120 g), and 3 mass % platinum-carbon (3.0 g) was added, followed by stirring in a hydrogen atmosphere at room temperature for 4 hours. Disappearance of the raw material was confirmed by HPLC, and then the catalyst was removed by filtration. Then, the filtrate was concentrated and dried to obtain DA-E (pale yellow liquid, amount obtained: 25 g, yield: 98%).

$^1$H NMR (DMSO-d$_6$): δ 6.86 (d, J=8.0 Hz, 2H, C$_6$H$_4$), 6.75 (d, J=8.0 Hz, 2H, C$_6$H$_4$), 6.48 (d, J=8.0 Hz, 2H, C$_6$H$_4$), 6.44 (d, J=8.0 Hz, 2H, C$_6$H$_4$), 4.98 (s, 2H, NH$_2$), 4.83 (s, 2H, NH$_2$), 4.13 (s, 2H, CH$_2$), 3.56 (s, 3H, CH$_3$), 3.13 (br, 2H, CH$_2$), 2.51 (br, 2H, CH$_2$). $^{13}$C{$^1$H} NMR (DMSO-d$_6$): δ 156.7, 148.3, 147.2, 129.4, 129.3, 128.9, 126.3, 125.2, 114.5, 114.3, 52.7, 49.9, 47.9, 33.8, 33.1, 155.4, 154.9, 148.2, 147.2, 129.5, 129.3, 129.1, 128.9, 126.6, 125.7, 114.5, 114.3, 78.9, 78.8, 50.2, 49.2, 48.4, 33.9, 33.3, 28.5 (each s).

Preparation Example 10

Preparation of aromatic diamine (DA-F): N-tert-ethoxycarbonyl-N-(2-(4-aminophenyl)ethyl)-N-(4-aminobenzyl)amine DA-F was prepared in the following two steps. DA-F corresponds to the specific diamine.

First Step: Preparation of N-tert-methoxycarbonyl-N-(2-(4-nitrophenyl)ethyl)-N-(4-nitrobenzyl)amine (DA-F-1)

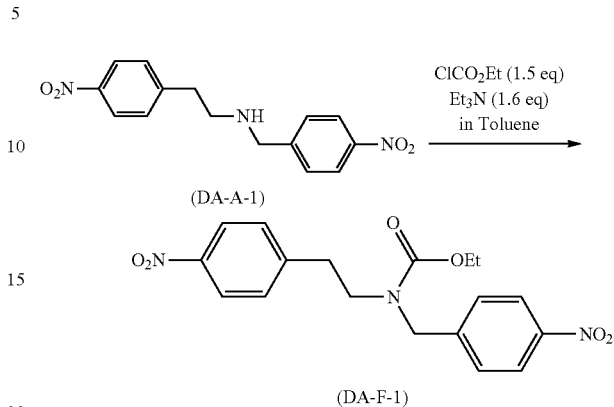

N-2-(4-Nitrophenyl)ethyl-N-4-nitrobenzylamine (30.0 g, 99.6 mmol) and triethylamine (16.1 g, 159 mmol) were added to toluene (300 g), the mixture was cooled to 5° C., and ethyl chloroformate (16.2 g, 149 mmol) was dropwise added over a period of 20 minutes. Then, the mixture was heated to 25° C. with stirring for one hour, and disappearance of the raw materials was confirmed by HPLC.

Then, the reaction mixture was heated to 60° C., and an operation of adding water (60 g) and disposing of the aqueous layer was repeated three times. Then, the organic layer was vacuum concentrated at 50° C., and the residue was mixed with toluene (270 g), heated to 60° C. and dissolved. Then, seed crystals (175 mg) were added at 25° C., the mixture was cooled to 5° C., followed by stirring for 18 hours, and the precipitated solid was collected by filtration. The solid was washed with a toluene/n-heptane mixture (3/2 (wt/wt), 50 g) cooled to 5° C., and dried to obtain N-ethoxycarbonyl-N-(2-(4-nitrophenyl)ethyl)-N-(4-nitrobenzyl)amine (DA-F-1) (white powder, amount obtained: 35 g, yield: 93%).

$^1$H NMR (DMSO-d$_6$): δ 8.20 (d, J=8.8 Hz, 2H, C$_6$H$_4$), 8.16 (d, J=8.8 Hz, 2H, C$_6$H$_4$), 7.50 (br, 4H, C$_6$H$_4$), 4.58 (s, 2H, CH$_2$), 4.01 (t, J=6.4 Hz, 2H, CH$_2$), 3.54 (br, 2H, CH$_2$), 2.98 (t, J=6.4 Hz, 2H, CH$_2$), 1.11 (br, 3H, CH$_3$). $^{13}$C{$^1$H} NMR (DMSO-d$_6$): δ 156.2, 147.8, 147.0, 146.8, 146.5, 130.5, 128.8, 128.5, 124.1, 124.0, 123.8, 123.5, 61.5, 49.9, 48.7, 48.1, 34.3, 33.8, 14.8 (each s).

Second Step: Preparation of N-tert-ethoxycarbonyl-N-(2-(4-aminophenyl)ethyl)-N-(4-aminobenzyl)amine (DA-F)

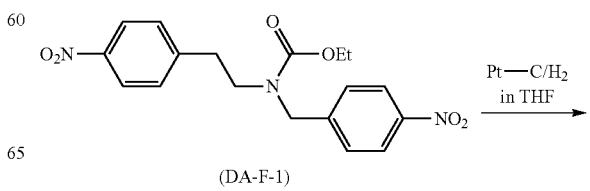

-continued

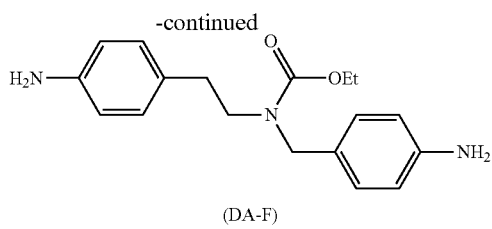

(DA-F)

N-Methoxycarbonyl-N-2-(4-nitrophenyl)ethyl-N-4-nitrobenzylamine (30.0 g, 80.4 mmol) was dissolved in tetrahydrofuran (120 g), and 3 mass % platinum-carbon (3.0 g) was added, followed by stirring in a hydrogen atmosphere at room temperature for 4 hours. Disappearance of the raw material was confirmed by HPLC, and then the catalyst was removed by filtration. Then, the filtrate was concentrated and dried to obtain DA-F (pale brown liquid, amount obtained: 25 g, yield: 99%).

$^1$H NMR (DMSO-$d_6$): δ 6.91 (d, J=7.6 Hz, 2H, $C_6H_4$), 6.79 (br, 2H, $C_6H_4$), 6.52 (d, J=8.4 Hz, 2H, $C_6H_4$), 6.48 (d, J=8.4 Hz, 2H, $C_6H_4$), 5.00 (s, 2H, $NH_2$), 4.85 (s, 2H, $NH_2$), 4.17 (s, 2H, $CH_2$), 4.04, (t, J=6.4 Hz, 2H, $CH_2$), 3.18 (br, 2H, $CH_2$), 2.53-2.48 (br, 2H, $CH_2$), 1.18 (t, J=7.0 Hz, 3H, $CH_3$). $^{13}C\{^1H\}$ NMR (DMSO-$d_6$): δ 156.2, 148.3, 147.2, 129.4, 129.2, 126.3, 125.3, 114.4, 114.2, 60.1, 49.7, 48.5, 47.9, 40.6, 33.8, 33.2, 15.0 (each s).

Preparation Example 11

Preparation of aromatic diamine (DA-G): N-isopropyloxycarbonyl-N-(2-(4-aminophenyl)ethyl)-N-(4-aminobenzyl)amine DA-G was prepared in the following two steps. DA-G corresponds to the specific diamine.

First Step: Preparation of N-isopropyloxycarbonyl-N-(2-(4-nitrophenyl)ethyl)-N-(4-nitrobenzyl)amine (DA-G-1)

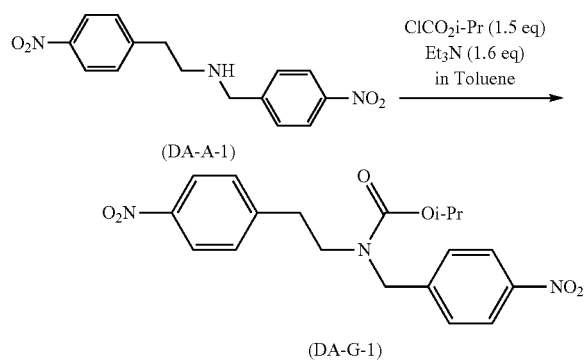

N-2-(4-Nitrophenyl)ethyl-N-4-nitrobenzylamine (30.0 g, 99.6 mmol) and triethylamine (16.2 g, 159 mmol) were added to toluene (300 g), followed by cooling to 5° C., and further isopropyl chloroformate (18.3 g, 149 mmol) was dropwise added over a period of one hour. Then, the mixture was stirred for one hour, and disappearance of the raw materials was confirmed by HPLC.

Then, water (60 g) and triethylamine (2.02 g, 20.0 mmol) were added to the reaction mixture, followed by stirring at 80° C. for 4 hours, to remove by-products into the aqueous layer. Then, the aqueous layer was disposed of at 60° C., and an operation of adding water (60 g) again, followed by stirring, and disposing of the aqueous layer, was repeated twice. Then, the organic layer was vacuum concentrated, and to the residue, toluene (150 g) and heptane (100 g) were added. Then, seed crystals (87.3 mg) were added, followed by stirring for 30 minutes, and heptane (50 g) was added, and the mixture was cooled from 25° C. to 5° C. Then, precipitated crystals were collected by filtration and dried to obtain N-isopropyloxycarbonyl-N-(2-(4-nitrophenyl)ethyl)-N-(4-nitrobenzyl)amine (DA-G-1) (white solid, amount obtained: 34.2 g, yield: 89%).

$^1$H NMR (DMSO-$d_6$): δ 8.21 (d, J=8.4 Hz, 2H, Ar), 8.16 (d, J=8.4 Hz, 2H, Ar), 7.52-7.50 (m, 4H, Ar), 4.77 (br 1H, CH), 4.58 (s, 2H, $CH_2$), 3.53 (br, 2H, $CH_2$), 2.97 (br, 2H, $CH_2$), 1.14 (br, 6H, $C(CH_3)_2$). $^{13}C\{^1H\}$ NMR (DMSO-$d_6$): δ 155.8, 147.8, 147.0, 146.9, 146.5, 130.5, 128.8, 128.6, 124.0, 123.8, 66.8, 49.8, 48.7, 48.0, 34.4, 33.9, 22.1 (each s).

Second Step: Preparation of N-isopropyloxycarbonyl-N-(2-(4-aminophenyl)ethyl)-N-(4-aminobenzyl)amine (DA-G)

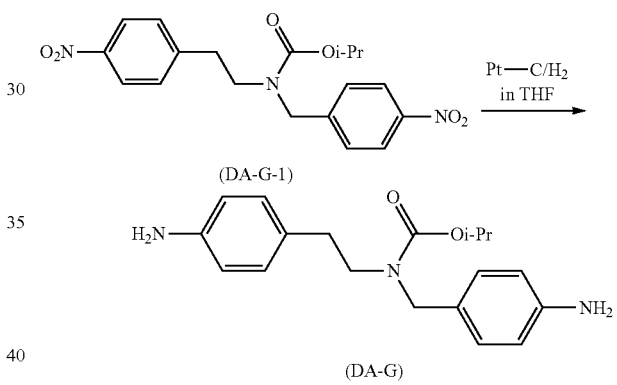

N-Isopropyloxycarbonyl-N-2-(4-nitrophenyl)ethyl-N-4-nitrobenzylamine (30.0 g, 77.4 mmol) was dissolved in tetrahydrofuran (120 g), 3 mass % platinum-carbon (3.0 g) was added, followed by stirring in a hydrogen atmosphere at room temperature for 4 hours. Disappearance of the raw material was confirmed by HPLC, and the catalyst was removed by filtration. Then, the filtrate was concentrated and dried to obtain DA-G (pale yellow liquid, amount obtained: 25.0 g, yield: 99%).

$^1$H NMR (DMSO-$d_6$): δ 6.88 (d, J=6.0 Hz, 2H, Ar), 6.76 (br, 2H, Ar), 6.51-6.44 (m, 4H, Ar), 4.97 (s, 2H, $NH_2$), 4.83 (s, 2H, $NH_2$), 4.77 (br, 1H, CH), 4.13 (s, 2H, $CH_2$), 3.14 (br, 2H, $CH_2$), 2.46 (br, 2H, $CH_2$), 1.16 (m, 6H, $C(CH_3)_2$). $^{13}C\{^1H\}$ NMR (DMSO-$d_6$): δ 155.7, 148.3, 147.2, 129.4, 129.2, 126.4, 125.4, 114.5, 114.2, 68.0, 49.7, 48.5, 47.9, 40.6, 33.8, 33.2, 22.4 (each s).

Preparation Example 12

Preparation of aromatic diamine (DA-H): N-benzyloxycarbonyl-N-(2-(4-aminophenyl)ethyl)-N-(4-aminobenzyl)amine DA-H was prepared in the following two steps. DA-H corresponds to the specific diamine.

First Step: Preparation of N-benzyloxycarbonyl-N-(2-(4-nitrophenyl)ethyl)-N-(4-nitrobenzyl)amine (DA-H-1)

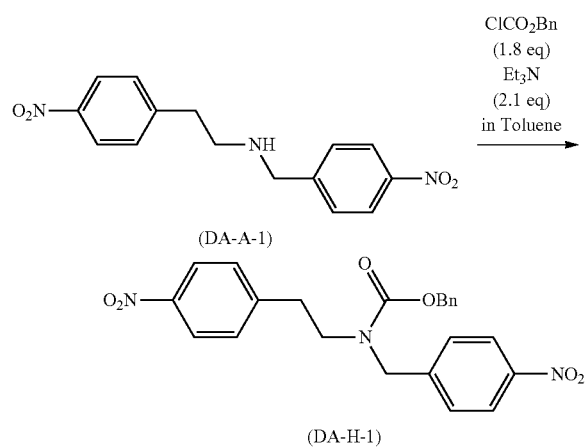

N-2-(4-Nitrophenyl)ethyl-N-4-nitrobenzylamine (3.00 g, 10.0 mmol) and triethylamine (1.61 g, 15.9 mmol) were added to toluene (30 g), the mixture was cooled 25 to 5° C., and benzyl chloroformate (2.21 g, 12.9 mmol) was dropwise added over a period of 25 minutes. 4 Hours later, triethylamine (0.55 g, 5.4 mmol) and benzyl chloroformate (0.92 g, 5.4 mmol) were further added, and one hour layer, triethylamine (0.04 g, 0.4 mmol) and benzyl chloroformate (0.04 g, 0.3 mmol) were further added, followed by stirring for 16 hours, and disappearance of the raw materials was confirmed by HPLC.

Then, water (6 g) was added to the reaction mixture, the mixture was heated to 60° C., and the aqueous layer was disposed of, and again, an operation of adding water (6 g), followed by stirring, and disposing of the aqueous layer, was repeated twice. Then, the organic layer was vacuum concentrated at 50° C., and the residue was mixed with toluene (15 g) and purified by silica gel column chromatography (eluent: toluene) to obtain N-benzyloxycarbonyl-N-(2-(4-nitrophenyl)ethyl)-N-(4-nitrobenzyl)amine (DA-H-1) (pale yellow liquid, amount obtained: 3.0 g, yield: 69%).

$^1$H NMR (DMSO-$d_6$): δ 8.15-8.00 (m, 4H, Ar), 7.48-7.07 (m, 9H, Ar), 5.01 (s, 2H, $CH_2$), 4.55 (s, 2H, $CH_2$), 3.52 (br, 2H, $CH_2$), 2.94-2.90 (br, 2H, $CH_2$). $^{13}$C{$^1$H}NMR(DMSO-$d_6$): δ 156.2, 155.6, 147.6, 147.1, 146.8, 146.6, 137.0, 130.5, 129.3, 128.9, 128.9, 128.7, 128.6, 128.4, 128.3, 128.1, 127.9, 126.8, 125.7, 124.0, 123.8. 69.5, 67.1, 66.9, 50.0, 48.9, 48.2, 34.3, 33.8 (each s).

Second Step: Preparation of N-benzyloxycarbonyl-N-(2-(4-aminophenyl)ethyl)-N-(4-aminobenzyl)amine (DA-H)

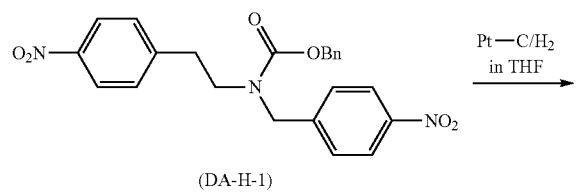

N-Benzyloxycarbonyl-N-2-(4-nitrophenyl)ethyl-N-4-nitrobenzylamine (1.0 g, 2.3 mmol) was dissolved in tetrahydrofuran (20 g) and 3 mass % platinum-carbon (0.1 g) was added, followed by stirring in a hydrogen atmosphere at room temperature for 7 hours. Disappearance of the raw material was confirmed by HPLC, and the catalyst was removed by filtration. Then, the filtrate was concentrated, mixed with n-heptane (15 g) and cooled to −40° C., the supernatant was removed, and the residue was dried to obtain DA-H (brown liquid, amount obtained: 0.79 g, yield: 92%).

$^1$H NMR (DMSO-$d_6$): δ 7.39-7.30 (m, 5H, Ar), 6.96-6.71 (br, 4H, Ar), 6.52-6.45 (m, 4H, Ar), 5.12-5.09 (m, 2H, $NH_2$), 5.02 (s, 2H, $NH_2$), 4.87 (s, 2H, $CH_2$), 4.20, (s, 2H, $CH_2$), 3.21 (br, 2H, $CH_2$), 2.51 (br, 2H, $CH_2$). $^{13}$C{$^1$H} NMR (DMSO-$d_6$): δ 156.1, 155.5, 148.4, 147.3, 137.5, 129.4, 129.3, 128.9, 128.8, 128.6, 128.2, 127.9, 126.2, 125.1, 114.5, 114.3 69.5, 66.6, 49.9, 48.7, 48.1, 33.8, 33.1 (each s).

Preparation Example 13

An aromatic diamine (DA-I) was prepared in the following two steps. DA-1 corresponds to the specific diamine.

First Step: Preparation of N-(9-fluorenyl)methyloxycarbonyl-N-(2-(4-nitrophenyl)ethyl)-N-(4-nitrobenzyl)amine (DA-I-1)

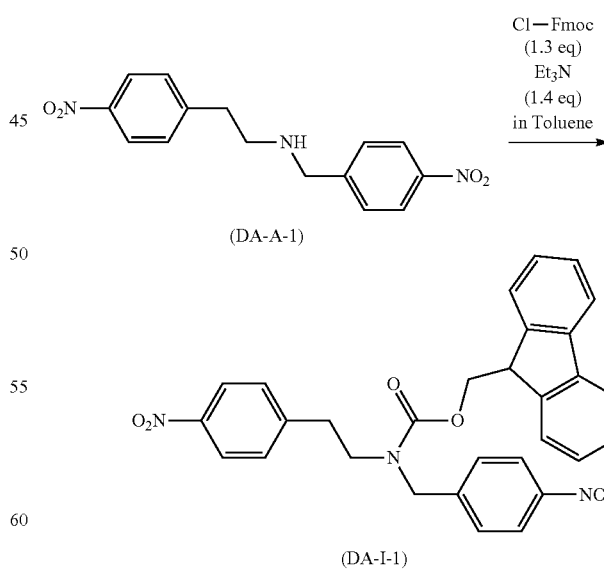

N-2-(4-Nitrophenyl)ethyl-N-4-nitrobenzylamine (2.0 g, 6.6 mmol) and triethylamine (0.94 g, 9.3 mmol) were added to toluene (20 g), the mixture was cooled to 5° C., and 9-fluorenylmethyl chloroformate (2.23 g, 8.62 mmol) was dropwise added over a period of 10 minutes. The mixture was stirred for 30 minutes, and disappearance of the raw materials was confirmed by HPLC.

Then, the reaction mixture was mixed with water (4 g) and heated to 60° C., and the aqueous layer was disposed of, and again, an operation of adding water (6 g), followed by stirring, and disposing of the aqueous layer, was repeated twice. Then, the organic layer was dried over magnesium sulfate, and the solvent was distilled off under reduced pressure. The residue was mixed with toluene (8 g), purified by silica gel column chromatography (eluent: toluene/ethyl acetate=10/0 to 10/1 (v/v) and evaporated to dryness. Then, the residue was mixed with isopropyl alcohol (79.6 g) and dissolved at 80° C., and the solution was cooled to 25° C., and the precipitated crystals were collected by filtration and dried to obtain N-(9-fluorenyl)methyloxycarbonyl-N-(2-(4-nitrophenyl)ethyl)-N-(4-nitrobenzyl)amine (DA-I-1) (white solid, amount obtained: 2.85 g, yield: 85%).

$^1$H NMR (DMSO-$d_6$): δ 8.18-7.00 (m, 16H, Ar), 4.78, 4.54 (d, J=4.0 Hz, 2H, $CH_2$), 4.42, 4.22 (s, 2H, $CH_2$), 4.32, 4.22 (s, 1H, CH), 3.48, 2.99 (br, 2H, $CH_2$), 2.89, 2.41 (br, 2H, $CH_2$). $^{13}$C{$^1$H} NMR(DMSO-d): δ 156.0, 155.6, 147.9, 147.1, 147.0, 146.5, 146.5, 144.4, 144.2, 141.4, 130.4, 130.3, 128.6, 128.0, 127.6, 127.4, 127.2, 125.1, 125.0, 123.9, 123.7, 123.6, 120.6, 66.0, 65.9, 50.2, 48.4, 47.7, 34.0, 33.7 (each s).

Second Step: Preparation of N-(9-fluorenyl)methyloxycarbonyl-N-(2-(4-aminophenyl)ethyl)-N-(4-aminobenzyl)amine (DA-I)

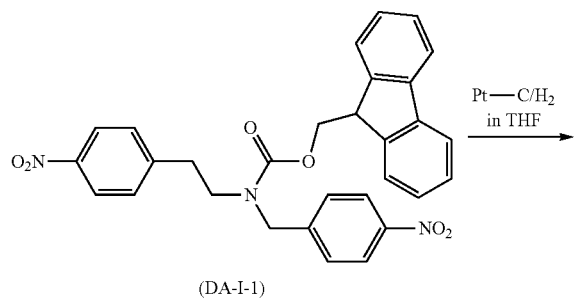

(DA-I-1)

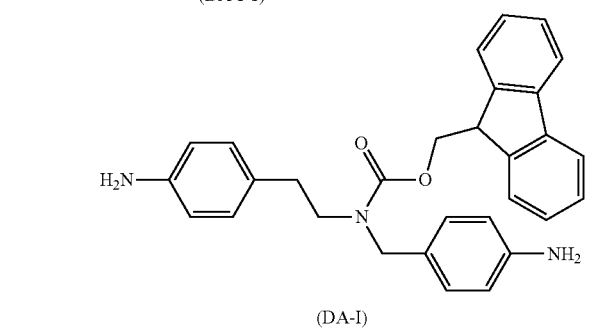

(DA-I)

N-(9-Fluorenyl)methyloxycarbonyl-N-2-(4-nitrophenyl)ethyl-N-4-nitrobenzylamine (1.0 g, 1.9 mmol) was dissolved in tetrahydrofuran (20 g), and 3 mass % platinum-carbon (0.1 g) was added, followed by stirring in a hydrogen atmosphere at room temperature for 6 hours. Disappearance of the raw material was confirmed by HPLC, and the catalyst was removed by filtration. The filtrate was concentrated and cooled to −5° C., and an operation of adding n-hexane (50 g) and removing the supernatant, was repeated three times.

Then, the residue was concentrated and dried to obtain DA-1 (white solid, amount obtained: 0.85 g, yield: 95%).

$^1$H NMR (DMSO-$d_6$): δ 7.88 (d, J=7.6 Hz, 2H, $C_{13}H_8$), 7.67, 7.66 (d, J=6.8 Hz, 2H, $C_{13}H$), 7.41 (dd, J=7.6, 6.8 Hz, 2H, $C_{13}H_8$), 7.34 (dd, J=6.8, 6.8 Hz, 2H, $C_{13}H_8$), 6.77, 6.58 (d, 8.0 Hz, 2H, $C_6H_4$), 6.48-6.41 (m, 6H, $C_6H_4$), 4.99 (s, 2H, $NH_2$), 4.84 (s, $NH_2$), 4.60, 4.51 (d, J=4.8 Hz, 2H, $CH_2$), 4.28 (t, J=4.8 Hz, 1H, CH), 4.09, 3.90 (s, 2H, $CH_2$), 3.12, 2.80 (t, J=7.0 Hz, 2H, $CH_2$), 2.44, 2.10 (t, J=7.0 Hz, 2H, $CH_2$). $^{13}$C{$^1$H} NMR (DMSO-$d_6$): δ 156.0, 155.4, 148.3, 147.2, 144.5, 141.4, 139.9, 137.9, 129.4, 129.1, 127.9, 127.7, 127.5, 126.3, 126.1, 125.3, 125.1, 121.8, 120.5, 116.7, 114.5, 114.4, 114.3, 114.2, 114.1, 110.2, 67.5, 66.5, 65.9, 49.9, 49.6, 48.7, 48.1, 47.6, 47.3, 35.5, 33.0, 31.4, 30.9, 25.6, 22.5 each s).

Preparation Example 14

Aromatic diamine (DA-J) was prepared in the following three steps. DA-J corresponds to the specific diamine.

First Step: Preparation of N-tert-butoxycarbonyldiethanolamine (DA-J-1)

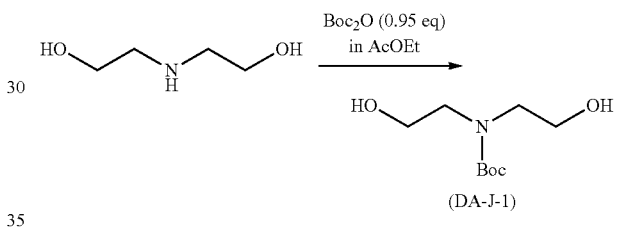

Diethanolamine (20.0 g, 190 mmol) was dissolved in ethyl acetate (60.0 g), and di-tert-butyl dicarbonate (39.4 g, 180 mmol) was dropwise added at 25° C. over a period of 20 minutes, followed by stirring for one hour. Disappearance of the raw materials was confirmed by gas chromatography, the reaction solution was subjected to a silica gel column (eluent: ethyl acetate), concentrated and dried to obtain N-tert-butoxycarbonyldiethanolamine (DA-J-1) (colorless liquid, amount obtained: 35.4 g, yield: 92%).

Second Step: Preparation of N-tert-butoxycarbonyl-N,N-bis(2-(4-nitrophenyloxy)ethyl)amine (DA-J-2)

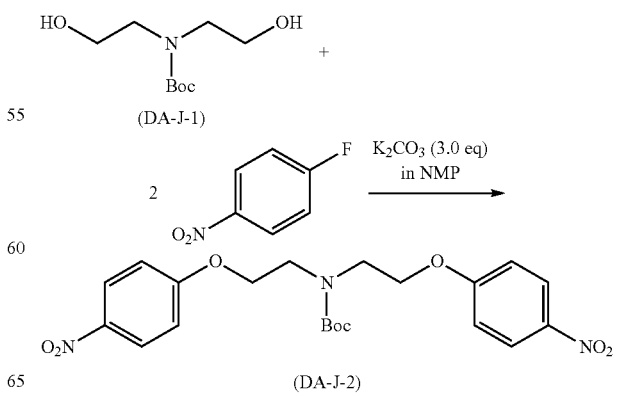

(DA-J-2)

N-tert-Butoxycarbonyldiethanolamine (20.0 g, 97.4 mmol) and 4-fluoronitrobenzene (33.0 g, 239 mmol) were dissolved in NMP (200 g), and potassium carbonate (40.4 g, 292 mmol) was further added, followed by stirring at 100° C. for 43 hours. Completion of the reaction was confirmed by HPLC, the reaction mixture was poured into water (2,000 g), and the precipitate was collected by filtration. Then, methanol (400 g) was added to the precipitate, followed by stirring. Then, the precipitate was collected by filtration, methanol (300 g) was added again, followed by stirring, and the precipitate was collected by filtration and dried to obtain N-tert-butoxycarbonyl-N, N-bis(2-(4-nitrophenyloxy)ethyl) amine (DA-J-2) (brown solid, amount obtained: 36.9 g, yield: 85%).

$^1$H NMR (DMSO-d$_6$): δ 8.10 (d, J=8.8 Hz, 4H, C$_6$H$_4$), 7.06 (d, J=8.8 Hz, 4H, C$_6$H$_4$), 4.20-4.18 (m, 4H, CH$_2$), 3.61-3.59 (m, 4H, CH$_2$), 1.28 (s, 9H, t-Bu). $^{13}$C{$^1$H} NMR (DMSO-d$_6$): δ 164.0, 155.1, 141.3, 126.3, 115.4, 79.8, 67.3, 67.1, 47.0, 46.6, 28.3 (each s).

Third Step: Preparation of N-tert-butoxycarbonyl-N,N-bis(2-(4-aminophenyloxy)ethylamine (DA-J)

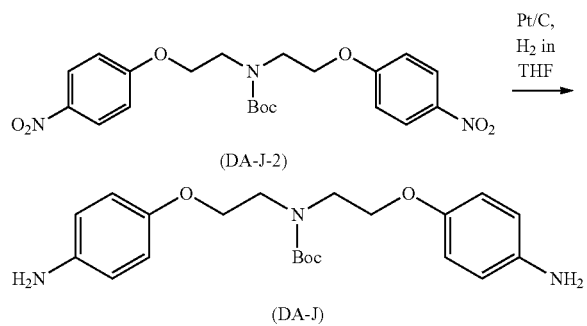

N-tert-Butoxycarbonyl-N,N-bis(2-(4-nitrophenyloxy) ethyl)amine (33.0 g, 73.7 mmol) was dissolved in THF (132 g), 3 mass % platinum-carbon (3.3 g) was added, followed by stirring in a hydrogen atmosphere at room temperature for 3 hours. Disappearance of the raw material was confirmed by HPLC, and the catalyst was removed by filtration. Then, the filtrate was concentrated, mixed with toluene (264 g), heated at 30° C. and dissolved. Then, the solution was cooled to 5° C., and the precipitated solid was collected by filtration and dried to obtain DA-J (pale brown solid, amount obtained: 25.6 g, yield: 90%).

$^1$H NMR (DMSO-d$_6$): δ 6.60 (d, J=8.4 Hz, 4H, C$_6$H$_4$), 6.46 (d, J=8.4 Hz, 4H, C$_6$H$_4$), 4.57 (s, 4H, NH$_2$), 3.90-3.87 (m, 4H, CH$_2$), 3.51-3.48 (m, 4H, CH$_2$), 1.35 (s, 9H, t-Bu). $^{13}$C{$^1$H} NMR (DMSO-d$_6$): δ 155.1, 150.0, 143.0, 115.7, 115.3, 79.4, 66.7, 47.7, 47.3, 28.4 (each s).

Preparation Example 15

Aromatic diamine (DA-K) was prepared in the following three steps. DA-K corresponds to the specific diamine.

First Step: Preparation of N-tert-butoxycarbonyl-4-nitrobenzylamine (DA-K-1)

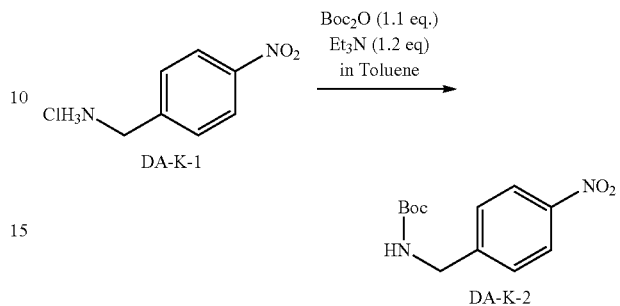

4-Nitrobenzylamine (5.00 g, 26.5 mmol) was suspended in toluene (50 g), triethylamine (3.22 g, 31.8 mmol) was added at room temperature, di-tert-butyl dicarbonate (6.36 g, 29.2 mmol) was dropwise added at room temperature over a period of 15 minutes, followed by stirring at 60° C. for 2 hours and at room temperature for 16 hours, and disappearance of the raw materials was confirmed by HPLC.

Then, an operation of adding water (20 g) at 60° C., followed by stirring, and disposing of the aqueous layer, was repeated twice, and then the organic layer was concentrated, the residue was mixed with toluene (15 g), heated to 60° C., mixed with heptane (15 g) and cooled to 5° C., followed by stirring for 16 hours, and the precipitated solid was collected by filtration and dried to obtain N-tert-butoxycarbonyl-4-nitrobenzylamine (white solid, amount obtained: 5.29 g, yield: 79%).

$^1$H NMR (DMSO-d$_6$): δ 8.21 (d, J=8.4 Hz, 2H, C$_6$H$_4$), 7.59 (t, J=5.8 Hz, 1H, NH), 7.51 (d, J=8.4 Hz, 2H, C$_6$H$_4$), 4.26 (d, J=5.8 Hz, 2H, CH$_2$), 1.40 (s, 9H, t-Bu)

Second Step: Preparation of N-tert-butoxycarbonyl-N-hydroxymethyl-4-nitrobenzylamine (DA-K-2)

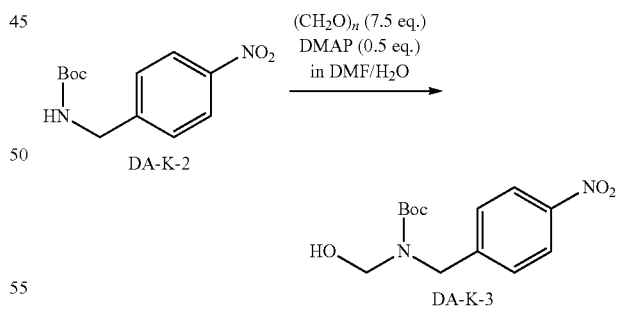

A mixed solution of N-tert-butoxycarbonyl-4-nitrobenzylamine (3.00 g, 11.9 mmol), paraformaldehyde (1.79 g, 59.5 mmol), 4-N,N-dimethylaminopyridine (0.73 g, 5.9 mmol), DMF (30 g) and water (6 g) was stirred at 60° C. for 7 hours, and paraformaldehyde (0.89 g, 29.6 mmol) was further added, followed by stirring for 15 hours.

Then, the reaction mixture was poured into water (300 g), ethyl acetate (200 g) was added, followed by stirring, the aqueous layer was disposed of, 1N hydrochloric acid (50 g) was added, followed by stirring, the aqueous layer was disposed, water (50 g) was added, followed by stirring, the aqueous layer was disposed of, and the organic layer was dried over magnesium sulfate.

Then, the organic layer was concentrated, purified by silica gel column chromatography (eluent: hexane/ethyl acetate=2/1 (v/v)), concentrated and dried to obtain N-tert-butoxycarbonyl-N-hydroxymethyl-4-nitrobenzylamine (colorless liquid, amount obtained: 2.60 g, yield: 77%).

$^1$H NMR (DMSO-d$_6$): δ 8.21 (d, J=8.0 Hz, 2H, C$_6$H$_4$), 7.56 (d, J=8.0 Hz, 2H, C$_6$H$_4$), 6.02 (br, 1H, OH), 4.74 (d, J=6.0 Hz, 2H, CH$_2$), 4.52 (s, 2H, CH$_2$), 1.27 (s, 9H, t-Bu). $^{13}$C{$^1$H} NMR (DMSO-d$_6$): δ 148.3, 146.9, 128.5, 123.8, 80.0, 79.8, 70.9, 49.3, 48.3, 28.2 (each s).

Third Step: Preparation of N-tert-butoxycarbonyl-N-(4-nitrophenyloxymethyl)-4-nitrobenzylamine (DA-K-4)

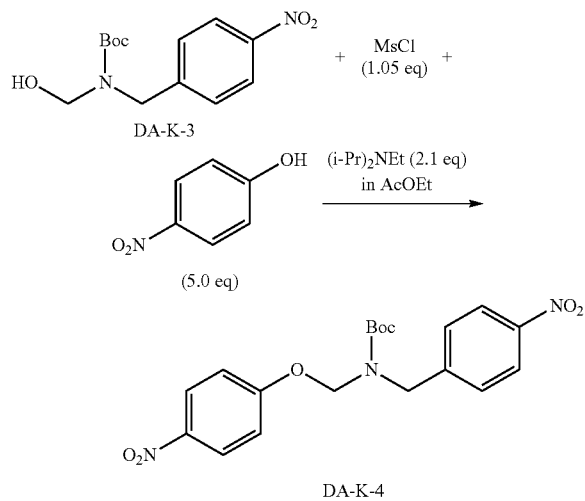

N-tert-Butoxycarbonyl-N-hydroxymethyl-4-nitrobenzylamine (142 mg, 0.50 mmol) was dissolved in ethyl acetate (0.50 g), diisopropylethylamine (71.4 mg, 0.55 mmol) was added, and methanesulfonyl chloride (60.4 mg, 0.53 mmol) was added at 0° C., followed by stirring for 30 minutes.

Then, the above reaction mixture was added at 5° C. to a mixture of 4-nitrophenol (349 mg, 2.5 mmol), ethyl acetate (1.0 g) and diisopropylethylamine (64.9 mg, 0.50 mmol), followed by stirring for 20 minutes.

Then, water (2 g) was added to the reaction mixture, the organic layer was washed with a 1N aqueous sodium hydroxide solution until no 4-nitrophenol was detected in the organic layer by HPLC, and finally, the organic layer was washed with water (2 g) and dried over magnesium sulfate.

Then, the organic layer was concentrated and purified by preparative thin layer chromatography (developing solvent: hexane/ethyl acetate=1/1 (v/v)) to obtain N-tert-butoxycarbonyl-N-(4-nitrophenyloxymethyl)-4-nitrobenzylamine (white solid, amount obtained: 47.2 mg, yield: 23%).

$^1$H NMR (DMSO-d$_6$): δ 8.19 (d, J=8.4 Hz, 4H, C$_6$H$_4$), 7.42 (d, J=8.0 Hz, 2H, C$_6$H$_4$), 7.08 (d, J=8.0 Hz, 2H, C$_6$H$_4$), 5.48 (s, 2H, CH$_2$), 4.65 (s, 2H, CH$_2$), 1.41 (s, 9H, t-Bu). $^{13}$C{$^1$H} NMR (DMSO-d$_6$): δ 154.5, 147.2, 145.3, 142.1, 128.4, 127.4, 125.9, 123.8, 115.4, 82.4, 75.8, 49.6, 49.2, 28.1 (each s).

Fourth Step: Preparation of N-tert-butoxycarbonyl-N-(4-aminophenyloxymethyl)-4-aminobenzylamine (DA-K)

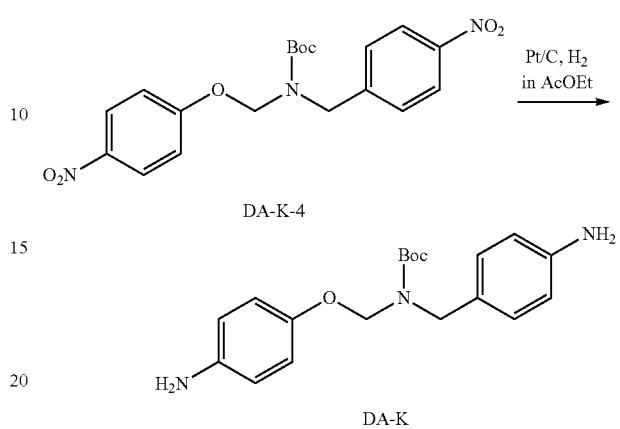

N-tert-Butoxycarbonyl-N-(4-nitrophenyloxymethyl)-4-nitrobenzylamine (47 mg, 0.12 mmol) was dissolved in ethyl acetate (10 g), and 3 mass % platinum-carbon (21 mg) was added, followed by stirring in a hydrogen atmosphere at room temperature for 4 hours. Disappearance of the raw material was confirmed by HPLC, the catalyst was removed by filtration, and the filtrate was concentrated and dried to obtain DA-K (colorless liquid, amount obtained: 36 mg, yield: 90%).

$^1$H NMR (CDCl$_3$): δ 7.01-7.04 (m, 2H, C$_6$H$_4$), 6.84-6.76 (m, 2H, C$_6$H$_4$), 6.64-6.59 (m, 4H, C$_6$H$_4$), 5.16, 5.04 (each s, 2H, CH$_2$), 4.47, 4.38 (each s, 2H, CH$_2$), 3.59 (br, 4H, NH$_2$), 1.45, 1.37 (each s, 9H, t-Bu). $^{13}$C{$^1$H} NMR (CDCl$_3$): δ 145.6, 129.6, 129.0, 119.4, 117.7, 116.4, 116.1, 115.1, 80.4, 75.1, 48.3, 47.5, 28.3, 28.3, 28.2 (each s).

Comparative Preparation Example 1

Preparation of aromatic diamine (DA-B): N-(2-(4-aminophenyl)ethyl)-N-(4-aminobenzyl)amine DA-B was prepared in the following two steps.

First Step: Preparation of N-(2-(4-nitrophenyl)ethyl)-N-(4-nitrobenzylidene)amine (DA-B-1)

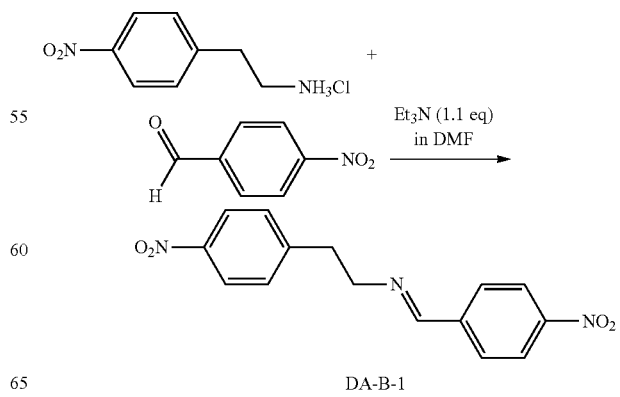

2-(4-Nitrophenyl)ethylamine hydrochloride (3.00 g, 19.9 mmol) was dissolved in DMF (15.0 g), 4-nitrobenzaldehyde (4.02 g, 19.9 mmol) was added, and further, triethylamine (2.21 g, 21.8 mmol) was added at 25° C. The mixture was stirred as it was at room temperature for 21 hours, and the resulting precipitate was collected by filtration. The precipitate was washed with water (50.0 g), subjected to filtration and vacuum dried at 50° C. to obtain N-(2-(4-nitrophenyl)ethyl)-N-(4-nitrobenzylidene)amine (white solid, amount obtained: 4.05 g, yield: 68%).

$^1$H NMR (DMSO-d$_6$): δ 8.45 (s, 1H, HC=N), 8.29 (d, J=8.8 Hz, 2H, C$_6$H$_4$), 8.16 (d, J=8.8 Hz, 2H, C$_6$H$_4$), 7.96, (d, J=8.8 Hz, 2H, C$_6$H$_4$), 7.57 (d, J=8.8 Hz, 2H, C$_6$H$_4$), 3.95 (t, J=7.0 Hz, 2H, CH$_2$), 3.13 (t, J=7.0 Hz, 2H, CH$_2$).

Melting point (DSC): 128° C.

Second Step: Preparation of N-(2-(4-aminophenyl)ethyl)-N-(4-aminobenzyl)amine (DA-B)

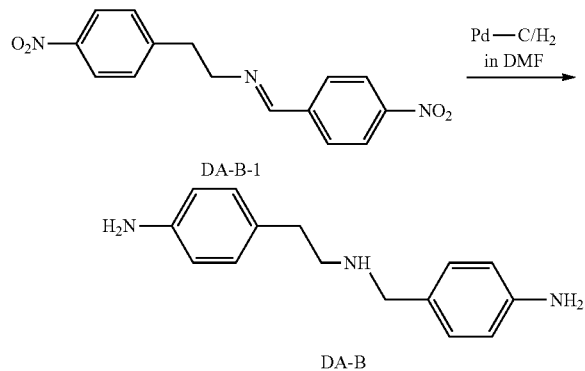

N-(2-(4-Nitrophenyl)ethyl)-N-(4-nitrobenzylidene)amine (3.50 g, 11.7 mmol) was added to DMF (35.0 g), and 5 mass % palladium-carbon (0.350 g) was added, followed by stirring in a hydrogen atmosphere at room temperature for 11 days. Disappearance of the raw material was confirmed by HPLC, and the catalyst was removed by filtration. Then, the filtrate was concentrated and dried to obtain DA-B as a brown oil (amount obtained: 2.82 g, yield: 100%).

$^1$H NMR (DMSO-d$_6$): δ 6.93 (d, J=8.0 Hz, 2H, C$_6$H$_4$), 6.82 (d, J=8.0 Hz, 2H, C$_6$H$_4$), 6.49 (d, J=8.0 Hz, 2H, C$_6$H$_4$), 6.47 (d, J=8.0 Hz, 2H, C$_6$H$_4$), 4.91-4.79 (m, 5H, NH$_2$, NH), 3.49 (br, 2H, CH$_2$), 2.69-2.42 (m, 4H, CH$_2$×2).

Comparative Preparation Example 2

Into a 30 mL two-necked flask, 0.723 g (3.00 mmol) of DA-B was weighed, and 9.30 g of NMP was added, followed by stirring while nitrogen was supplied to dissolve DA-B. 0.672 g (3.00 mmol) of 1,3-dimethyl-1,2,3,4-cyclobutanetetracarboxylic dianhydride was added to the resulting diamine solution with stirring, and 3.31 g of NMP was further added so that the solid content concentration would be 12 mass %. Then, the mixture was stirred at room temperature for one hour, whereupon the reaction solution gelated, and stirring was no longer possible.

INDUSTRIAL APPLICABILITY

The novel diamine of the present invention is useful as a material of a polyimide having an aliphatic secondary amino group by heating without gelating at the time of polymerization with tetracarboxylic acid.

The entire disclosures of Japanese Patent Application No. 2013-220592 filed on Oct. 23, 2013, Japanese Patent Application No. 2013-273459 filed on Dec. 27, 2013 and Japanese Patent Application No. 2014-186809 filed on Sep. 12, 2014 including specifications, claims and summaries are incorporated herein by reference in their entireties.

The invention claimed is:

1. A diamine represented by the formula (1):

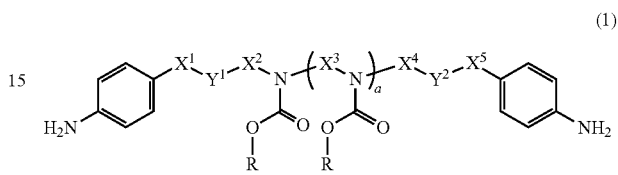

wherein each of X$^1$ and X$^5$ is independently a single bond, —CH$_2$— or —CH$_2$CH$_2$—, each of X$^2$ and X$^4$ is independently —CH$_2$— or —CH$_2$CH$_2$—, X$^3$ is a C$_{1-6}$ alkylene or cyclohexylene, each of Y$^1$ and Y$^2$ is independently a single bond, —O—, —NH—, —N(CH$_3$)—, —C(=O)—, —C(=O)O—, —C(=O)NH—, —C(=O)N(CH$_3$)—, —OC(=O)—, —NHC(=O)— or —N(CH$_3$)C(=O)—, R is a C$_{1-20}$ linear, branched or cyclic hydrocarbon group, and a is 0 or 1.

2. The diamine of claim 1, wherein in the formula (1), each of X$^1$ and X$^5$ is independently a single bond or —CH$_2$—.

3. The diamine of claim 1, wherein in the formula (1), each of X$^2$ and X$^4$ is independently —CH$_2$—.

4. The diamine of claim 1, wherein in the formula (1), each of Y$^1$ and Y$^2$ is independently a single bond or —O—.

5. The diamine of claim 1, wherein in the formula (1), Y$^1$ and Y$^2$ are symmetrical.

6. The diamine of claim 1, wherein in the formula (1), a is 0.

7. The diamine of claim 1, wherein in the formula (1), R is a t-butyl group or a 9-fluorenylmethyl group.

8. The diamine of claim 1, wherein in the formula (1), each of Y$^1$ and Y$^2$ is a single bond.

9. The diamine of claim 1, which is represented by the formula (2), (1-1), (1-6), (1-21), (1-26), (1-33), (1-34), (1-35), (1-36) or (1-38):

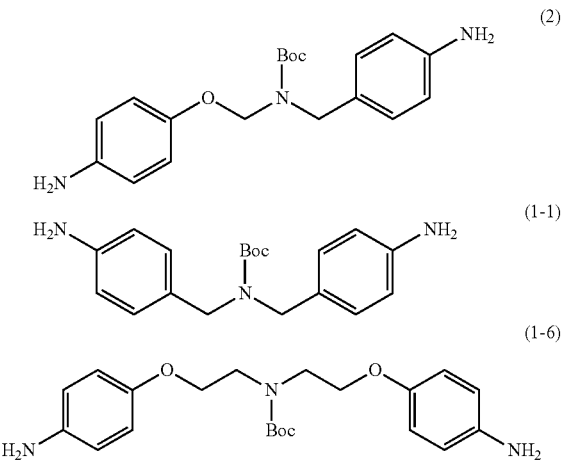

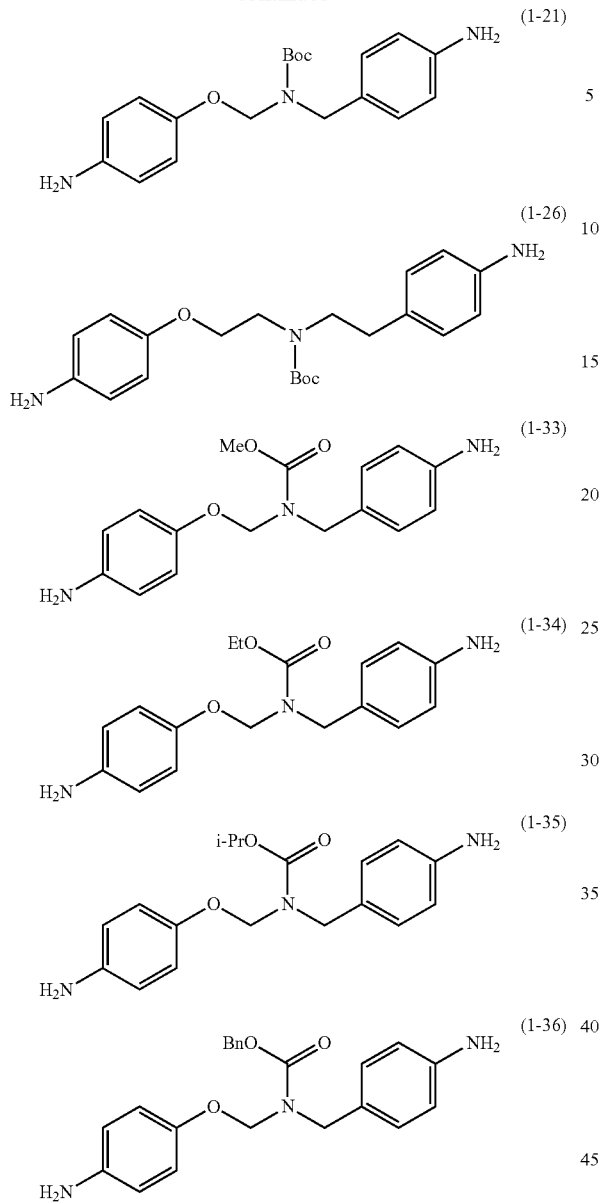

(1-21)
(1-26)
(1-33)
(1-34)
(1-35)
(1-36)

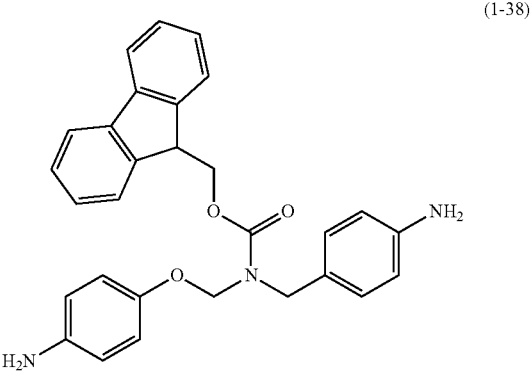

(1-38)

wherein Boc represents a tert-butoxycarbonyl group.

10. A polyimide precursor, obtained by a process comprising subjecting a diamine component comprising a diamine and a tetracarboxylic acid derivative to polycondensation,
wherein the diamine is represented by the formula (1)

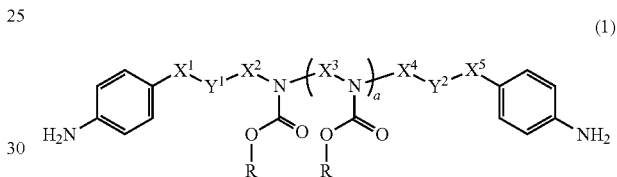

(1)

wherein each of $X^1$ and $X^5$ is independently a single bond, —$CH_2$— or —$CH_2CH_2$—, each of $X^2$ and $X^4$ is independently —$CH_2$— or —$CH_2CH_2$—, $X^3$ is a $C_{1-6}$ alkylene or cyclohexylene, each of $Y^1$ and $Y^2$ is independently a single bond, —O—, —NH—, —N($CH_3$)—, —C(=O)—, —C(=O)O—, —C(=O)NH—, —C(=O)N($CH_3$)—, —OC(=O)—, —NHC(=O)— or —N($CH_3$)C(=O)—, R is a $C_{1-20}$ linear, branched or cyclic hydrocarbon group, and a is 0 or 1.

11. The polyimide precursor of claim 10, wherein the diamine component comprises the diamine in an amount of from 20 to 100 mol %.

12. A polyimide obtained by imidizing the polyimide precursor as defined in claim 10.

* * * * *